(12) United States Patent
Cole et al.

(10) Patent No.: US 12,369,917 B1
(45) Date of Patent: Jul. 29, 2025

(54) SYSTEMS AND METHODS FOR MULTI-WAY ANASTOMOTIC COUPLING

(71) Applicant: Dignity Health, San Francisco, CA (US)

(72) Inventors: Tyler Cole, San Francisco, CA (US); Dakota Graham, San Francisco, CA (US)

(73) Assignee: Dignity Health, San Francisco, CA (US)

(*) Notice: Subject to any disclaimer, the term of this patent is extended or adjusted under 35 U.S.C. 154(b) by 660 days.

(21) Appl. No.: 17/568,300

(22) Filed: Jan. 4, 2022

Related U.S. Application Data

(60) Provisional application No. 63/226,953, filed on Jul. 29, 2021, provisional application No. 63/133,445, filed on Jan. 4, 2021.

(51) Int. Cl.
*A61B 17/11* (2006.01)
*A61B 17/00* (2006.01)

(52) U.S. Cl.
CPC ..... *A61B 17/11* (2013.01); *A61B 2017/00477* (2013.01); *A61B 2017/1107* (2013.01); *A61B 2017/1135* (2013.01)

(58) Field of Classification Search
CPC ..... A61B 17/11–115; A61B 2017/1103–1157; A61B 17/28–295
USPC ........ 606/146, 148, 149, 150, 151, 153, 219
See application file for complete search history.

(56) References Cited

U.S. PATENT DOCUMENTS

| | | | | |
|---|---|---|---|---|
| 3,496,939 A | * | 2/1970 | Odiaga | A61B 17/1114 606/154 |
| 4,233,981 A | * | 11/1980 | Schomacher | A61B 17/11 606/153 |
| 4,523,592 A | * | 6/1985 | Daniel | A61B 17/11 606/153 |
| 4,624,257 A | * | 11/1986 | Berggren | A61B 17/11 606/153 |
| 2010/0063520 A1 | * | 3/2010 | Bilotti | A61B 17/1114 606/153 |
| 2010/0114292 A1 | * | 5/2010 | Heaton | A61F 2/064 623/1.36 |
| 2021/0038241 A1 | * | 2/2021 | Brasset | A61B 34/37 |

* cited by examiner

*Primary Examiner* — Kathleen S Holwerda
*Assistant Examiner* — Serenity A Miller
(74) *Attorney, Agent, or Firm* — Polsinelli PC

(57) ABSTRACT

The multi-way coupler ring assembly is configured to couple a first end of a receiving vessel with a second end of the receiving vessel, and is further configured to couple a donor vessel to the first and second ends of the receiving vessel in a three-way junction. The multi-way coupler ring assembly includes a first receiving coupler ring configured to receive a first receiving vessel and a second receiving coupler ring configured to receive a second receiving vessel and couple with the first receiving coupler ring. The multi-way coupler ring assembly further includes a donor coupler ring configured to receive the donor vessel and couple with the first receiving coupler ring and the second receiving coupler ring. The first receiving coupler ring, the second receiving coupler ring and the donor coupler ring each respectively define a wedged face to enable three-way simultaneous or stepwise coupling with one another.

23 Claims, 23 Drawing Sheets

SYSTEMS AND METHODS FOR MULTI-WAY ANASTOMOTIC COUPLING

CROSS-REFERENCE TO RELATED APPLICATIONS

This is a non-provisional application that claims benefit to U.S. Provisional Patent Application Ser. No. 63/133,445 filed 4 Jan. 2021 and to U.S. Provisional Patent Application Ser. No. 63/226,953 filed 29 Jul. 2021, which are herein incorporated by reference in their entireties.

FIELD

The present disclosure generally relates to vessel coupling systems, and in particular, to a system and associated method for three-way coupling of vessels within the body for end-to-side anastomosis.

BACKGROUND

Microvascular anastomotic coupling is a technique for joining small blood vessels (1 mm-4 mm in size) that was developed in the 1980s. Usage of this technique to join small vessel in surgical procedures has increased since that time. This contrasts with traditional microvascular anastomosis involving the manual use of small sutures. Devices to perform microvascular coupling have been studied extensively in a number of surgical fields, including plastic surgery and head and neck surgery. A major limitation for these devices is that they are designed for end-to-end joining of blood vessels. No current designs are designed specifically to perform end-to-side anastomosis, which involves connecting the free end of a donor vessel into the side of a recipient vessel through an arteriotomy (incision or opening).

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Various embodiments of a multi-way coupler ring assembly for coupling a donor vessel to a receiving vessel are described herein. The multi-way coupler ring assembly enables end-to-side anastomosis through severing a receiving vessel to form a first receiving vessel and a second receiving vessel that are subsequently joined in a three-way connection with the donor vessel using the multi-way coupler ring assembly. In particular, the multi-way coupler ring assembly is configured to couple a first end of a receiving vessel with a second end of the receiving vessel, and is further configured to couple a donor vessel to the first and second ends of the receiving vessel in a three-way junction. The multi-way coupler ring assembly includes a first receiving coupler ring configured to receive a first receiving vessel and a second receiving coupler ring configured to receive a second receiving vessel and couple with the first receiving coupler ring. The multi-way coupler ring assembly further includes a donor coupler ring configured to receive the donor vessel and couple with the first receiving coupler ring and the second receiving coupler ring. The first receiving coupler ring, the second receiving coupler ring and the donor coupler ring each respectively define a wedged face to enable three-way simultaneous or stepwise coupling with one another.

Figure 1:
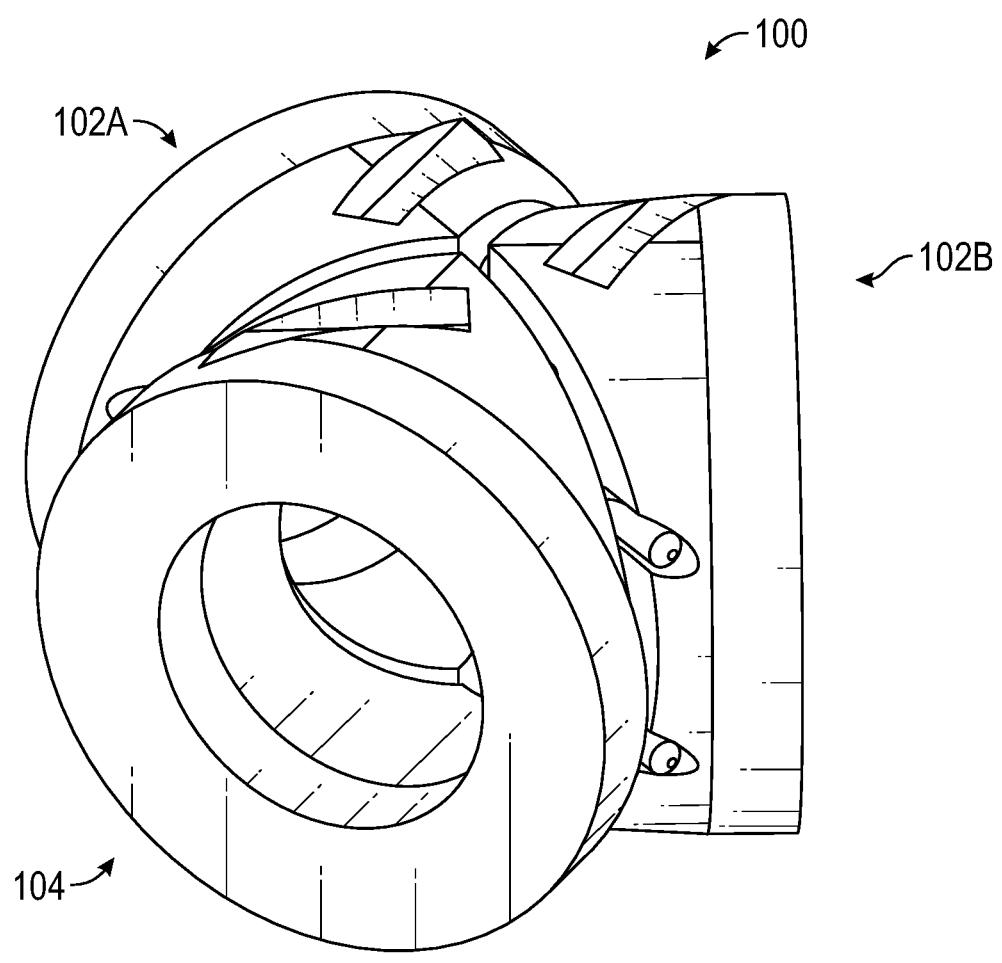
FIG. 1 is an illustration showing a perspective view of a multi-way coupler ring assembly that enables end-to-side anastomosis.

Referring to FIG. 1, a first embodiment of a multi-way coupler ring assembly 100 is illustrated that enables end-to-side anastomosis between a receiving vessel and a donor vessel. In particular, the multi-way coupler ring assembly 100 includes a first receiving coupler ring 102A and a second receiving coupler ring 102B that couple a first portion of a receiving vessel (first receiving vessel 2A in FIG. 7C) with a second portion of a second receiving vessel (second receiving vessel 2B in FIG. 7C) when the receiving vessels are respectively engaged with the first receiving coupler ring 102A and the second receiving coupler ring 102B. The multi-way coupler ring assembly 100 further includes a donor coupler ring 104 that couples with the first receiving coupler ring 102A and the second receiving coupler ring 102B to connect a donor vessel 3 (FIG. 7C) to the first receiving vessel 2A and the second receiving vessel 2B. As shown, the first receiving coupler ring 102A, the second receiving coupler ring 102B, and the donor coupler ring 104 define a wedged-shaped face that enables secure multi-way coupling of multiple vessels.

In some embodiments, the receiving vessel and the donor vessel can include any appropriate vessels within the body in which end-to-side anastomosis is required. For instance, vessels of the body for engagement with the multi-way coupler ring assembly 100 can include blood vessels, lymphatic vessels bowels, nerves, or other vessels within the body that can be sectioned and re-connected. Depending on the type of vessel to be coupled, sizes of the multi-way coupler ring assembly 100 can vary accordingly.

Figure 2A:
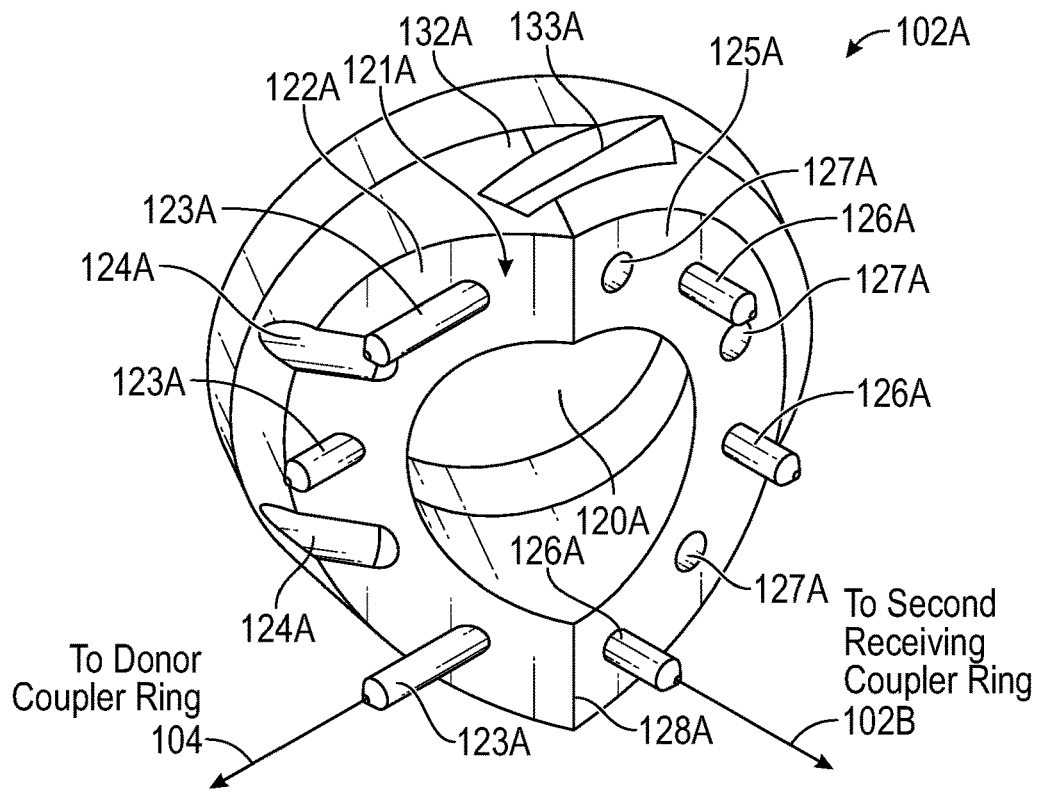
FIGS. 2A and 2B are respective illustrations showing perspective views of a first receiving coupler ring and a second receiving coupler ring of the multi-way coupler ring assembly of FIG. 1.
Figure 2B:
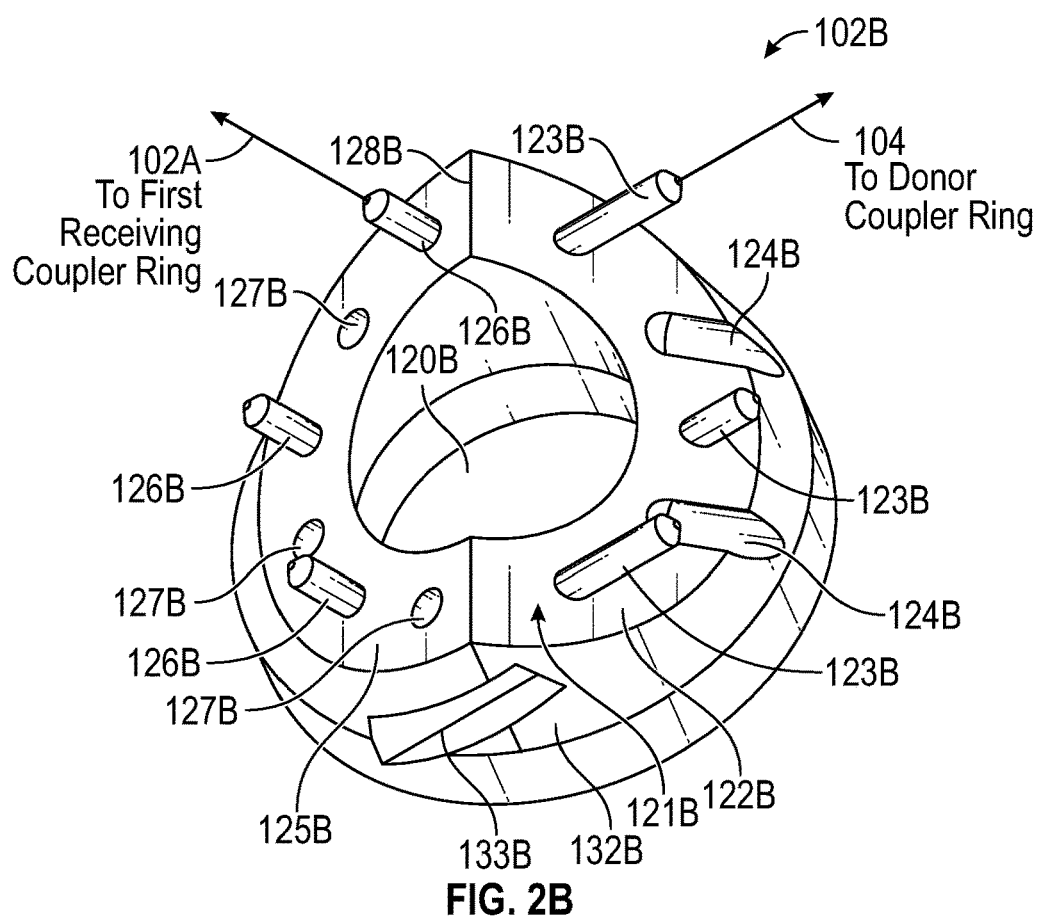
Figure 6:
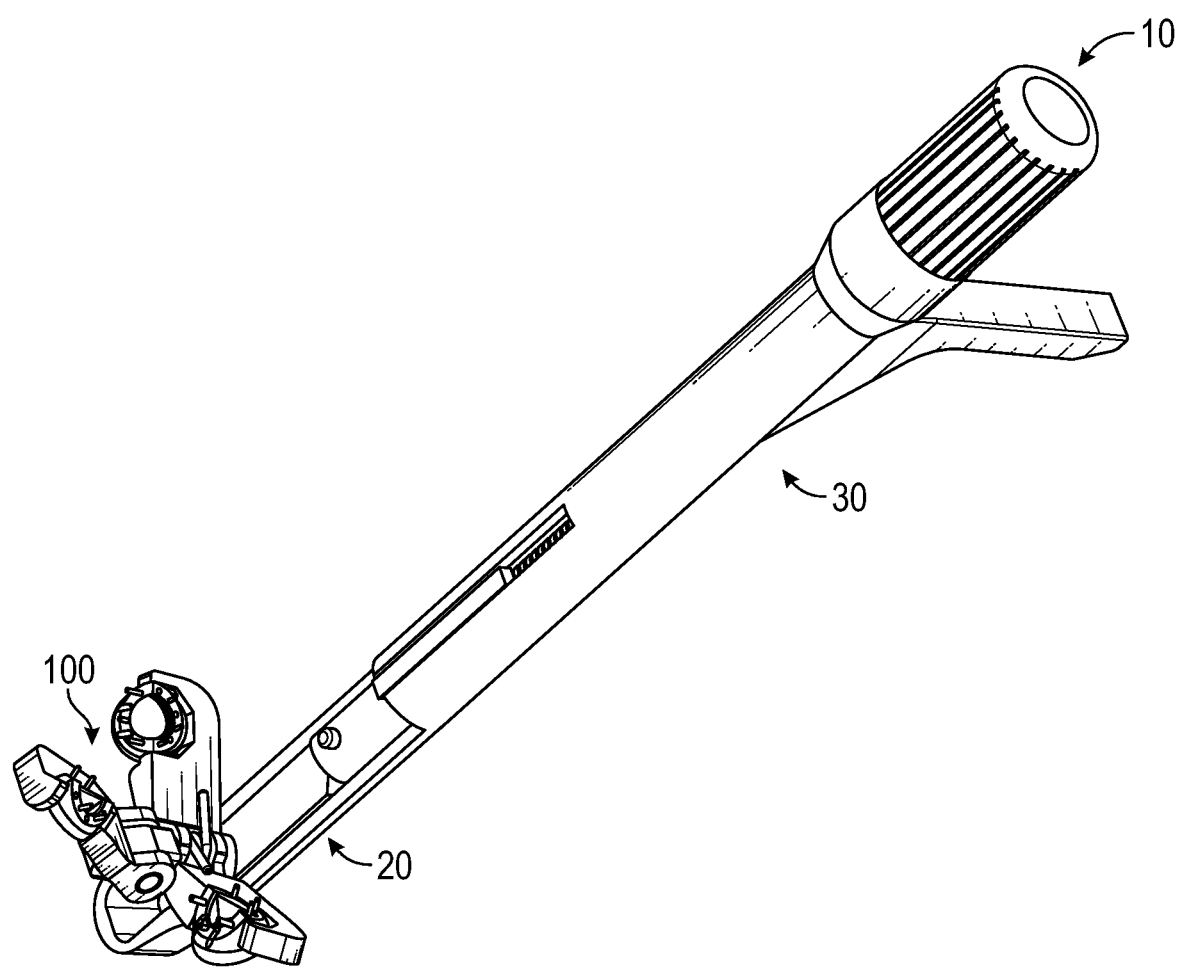
FIG. 6 is an illustration showing a perspective view of a coupler device for coupling the multi-way coupler ring assembly of FIG. 1.

In one embodiment shown in FIGS. 2A and 2B, the first receiving coupler ring 102A and the second receiving coupler ring 102B can be identical with the second receiving coupler ring 102B being rotated 180 degrees relative to the first receiving coupler ring 102A when coupling with the first receiving coupler ring 102A. Referring specifically to FIG. 2A, the first receiving coupler ring 102A is generally ring-shaped and defines a wedged face 121A for engagement with the second receiving coupler ring 102B and the donor coupler ring 104, and additionally includes a channel 120A for passage of a first receiving vessel 2A (FIG. 6C). As shown, the channel 120A of the first receiving coupler ring 102A defines an elliptical cross-section to reduce an eversion distance required of the first receiving vessel 2A. The wedged face 121A defines a first face 122A and an opposite second face 125A divided by an apex 128A that enables three-way engagement with the second receiving coupler ring 102B and the donor coupler ring 104. The first and second faces 122A and 125A of the first receiving coupler ring 102A each include a respective first and second plurality of pins 123A and 126A. In particular, the first face 122A includes a first plurality of pins 123A for engagement with the donor coupler ring 104 and the second face 125A includes a second plurality of pins 126A for engagement with the second receiving coupler ring 102B. As shown in FIG. 2A, the first plurality of pins 123A defined along the first face 122A of the first receiving coupler ring 102A are oriented towards the donor coupler ring 104. In contrast, the second plurality of pins 126A defined along the second face 125A of the first receiving coupler ring 102A are oriented perpendicular to the second face 125A of the first receiving coupler ring 102A as further shown in FIG. 2A. Additionally, the first and second plurality of pins 123A and 126A are also configured to capture an everted portion of the first receiving vessel 2A, as shown in FIG. 7C.

Likewise, the first and second faces 122A and 125A each include a respective first and second plurality of pin receptacles 124A and 127A. In particular, the first face 122A includes a first plurality of pin receptacles 124A for engagement with the donor coupler ring 104 and the second face 125A includes a second plurality of pin receptacles 127A for engagement with the second receiving coupler ring 102B. In the embodiment of FIG. 2A, the first plurality of pin receptacles 124A defined along the first face 122A of the first receiving coupler ring 102A are oriented towards the donor coupler ring 104. As shown, in some embodiments, the first plurality of pin receptacles 124A define a notched configuration to receive the donor coupler ring 104, and the second plurality of pin receptacles 127A define a channel configuration to receive the second receiving coupler ring 102B. The second plurality of pin receptacles 127A defined along the second face 125A of the first receiving coupler ring 102A are oriented perpendicular to the second face 125A of the first receiving coupler ring 102A as further shown in FIG. 2A.

Figure 7A:
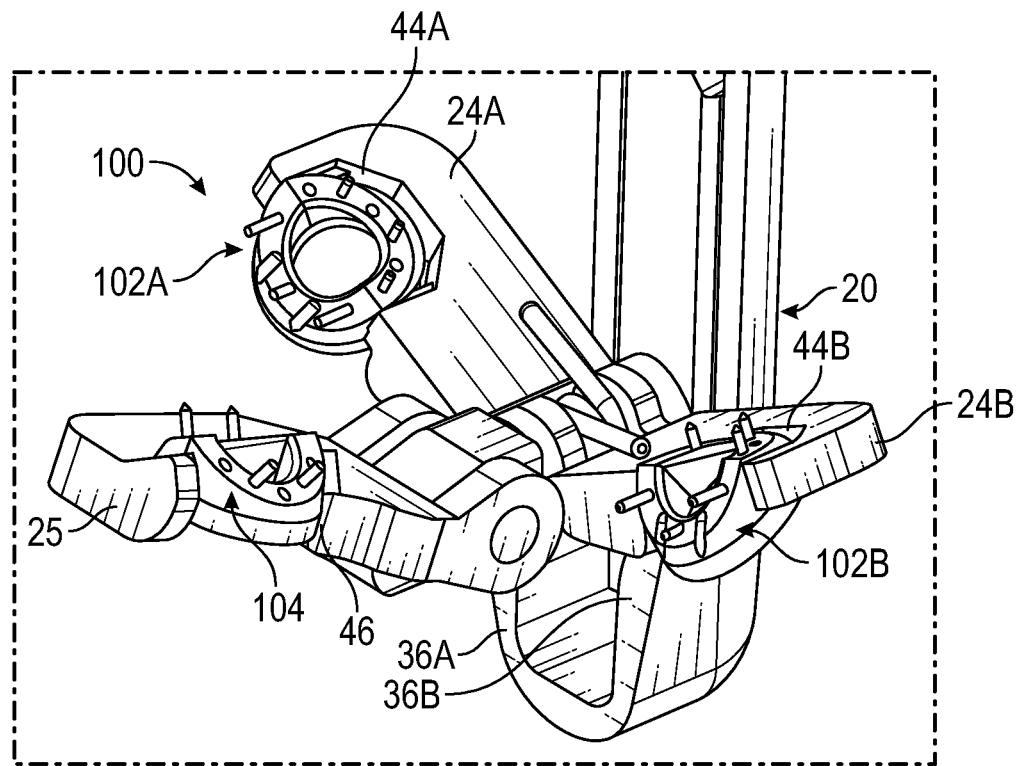
FIGS. 7A-7E are a series of illustrations showing engagement of the first receiving coupler ring, the second receiving coupler ring, and the donor ring of the multi-way coupler ring assembly of FIG. 1 using the coupler device of FIG. 6 and showing a first receiving vessel, a second receiving vessel and a donor vessel to be coupled by the multi-way coupler ring assembly of FIG. 1.

Further, the first receiving coupler ring 102A defines a peripheral surface 132A that includes a pair of slots 133A for engagement with a coupler device 20 (FIG. 7A). The first receiving coupler ring 102A additionally includes a rear face (not shown) defined opposite to the wedged face 121A. In the embodiment shown, the wedged face 121A defines a first angle between the first face 122A and the second face 125A, which is in some embodiments, may be a 120 degree angle; however, other angles are contemplated.

FIG. 2B illustrates the second receiving coupler ring 102B. The second receiving coupler ring 102B may be rotated 180 degrees relative to the first receiving coupler ring 102A when coupling with the first receiving coupler ring 102A and can be identical to the first receiving coupler ring 102A. The second receiving coupler ring 102B is generally ring-shaped and defines a wedged face 121B for engagement with the first receiving coupler ring 102A and the donor coupler ring 104, and additionally includes a channel 120B for passage of a second receiving vessel 2B (FIG. 7C). As shown, the channel 120B of the second receiving coupler ring 102B defines an elliptical cross-section to reduce an eversion distance required of the second receiving vessel. The wedged face 121B defines a first face 122B and an opposite second face 125B divided by an apex 128B that enables three-way engagement with the first receiving coupler ring 102A and the donor coupler ring 104. The first and second faces 122B and 125B of the second receiving coupler ring 102B each include a respective first and second plurality of pins 123B and 126B; in particular, the first face 122B includes a first plurality of pins 123B for engagement with the donor coupler ring 104 and the second face 125B includes a second plurality of pins 126B for engagement with the first receiving coupler ring 102A. As shown in FIG. 2B, the first plurality of pins 123B defined along the first face 122B of the second receiving coupler ring 102B are oriented towards the donor coupler ring 104. In contrast, the second plurality of pins 126B defined along the second face 125B of the second receiving coupler ring 102B are oriented perpendicular to the second face 125B of the second receiving coupler ring 102B as further shown in FIG. 2B. Additionally, the first and second plurality of pins 123B and 126B are also configured to capture an everted portion of the second receiving vessel 2B, as shown in FIG. 7C.

Likewise, the first and second faces 122B and 125B each include a respective first and second plurality of pin receptacles 124B and 127B. Specifically, the first face 122B includes a first plurality of pin receptacles 124B for engagement with the donor coupler ring 104 and the second face 125B includes a second plurality of pin receptacles 127B for engagement with the first receiving coupler ring 102A. In the embodiment of FIG. 2B, the first plurality of pin receptacles 124B defined along the first face 122B of the second receiving coupler ring 102B are oriented towards the donor coupler ring 104. As shown, in some embodiments, the first plurality of pin receptacles 124B define a notched configuration to receive the donor coupler ring 104, and the second plurality of pin receptacles 127B define a channel configuration to receive the second plurality of pins 126B of the first receiving coupler ring 102A. The second plurality of pin receptacles 127B defined along the second face 125B of the second receiving coupler ring 102B are oriented perpendicular to the second face 125A of the second receiving coupler ring 102B as further shown in FIG. 2B.

Further, the second receiving coupler ring 102B defines a peripheral surface 132B that includes a pair of slots 133B for engagement with the coupler device 20 (FIG. 7A). The second receiving coupler ring 102B additionally includes a rear face (not shown) defined opposite to the wedged face 121B. In the embodiment shown, the wedged face 121B defines a second angle between the first face 122B and the second face 125B which is in some embodiments a 120 degree angle; however other angles are contemplated.

Figure 3:
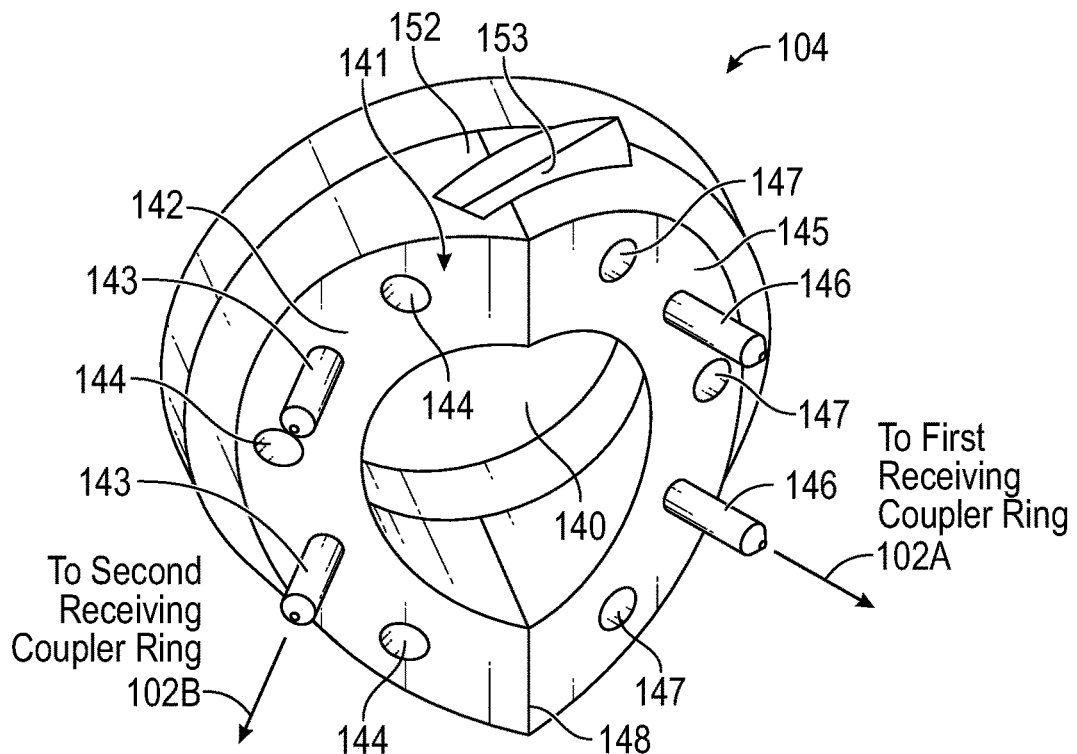
FIG. 3 is an illustration showing a perspective view of a donor coupler ring of the multi-way coupler ring assembly of FIG. 1.
Figure 4:
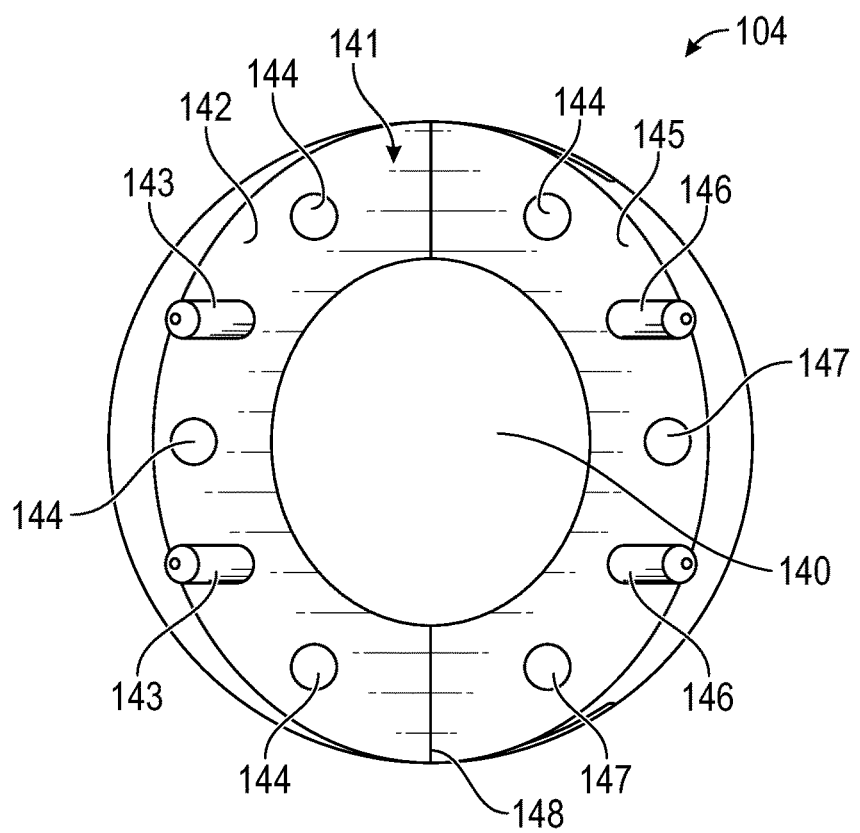
FIG. 4 is an illustration showing a front view of the donor coupler ring of FIG. 3.

FIG. 3 illustrates the donor coupler ring 104 that engages the first and second receiving coupler rings 102A and 102B. The donor coupler ring 104 is generally ring-shaped and defines a wedged face 141 for engagement with the first receiving coupler ring 102A and the second receiving coupler ring 102B and a channel 140 for passage of a donor vessel 3. As shown, the channel 140 of the donor coupler ring 104 defines an elliptical cross-section to reduce an eversion distance required of the donor vessel 3. The wedged face 141 defines a first face 142 and an opposite second face 145 divided by an apex 148 that enables three-way engagement with the first receiving coupler ring 102A and the second receiving coupler ring 102B. The first and second faces 142 and 145 include a respective first and second plurality of pins 143 and 146. In particular, the first face 142 includes a first plurality of pins 143 for engagement with the first plurality of pins 124B of the second receiving coupler ring 102B and the second face 145 includes a second plurality of pins 146 for engagement with the first plurality of pins 124B of the second receiving coupler ring 102B the first receiving coupler ring 102A. In addition, the first and second plurality of pins 143 and 146 are also configured to capture an everted portion of the donor vessel 3, as shown in FIG. 7C.

Figure 5A:
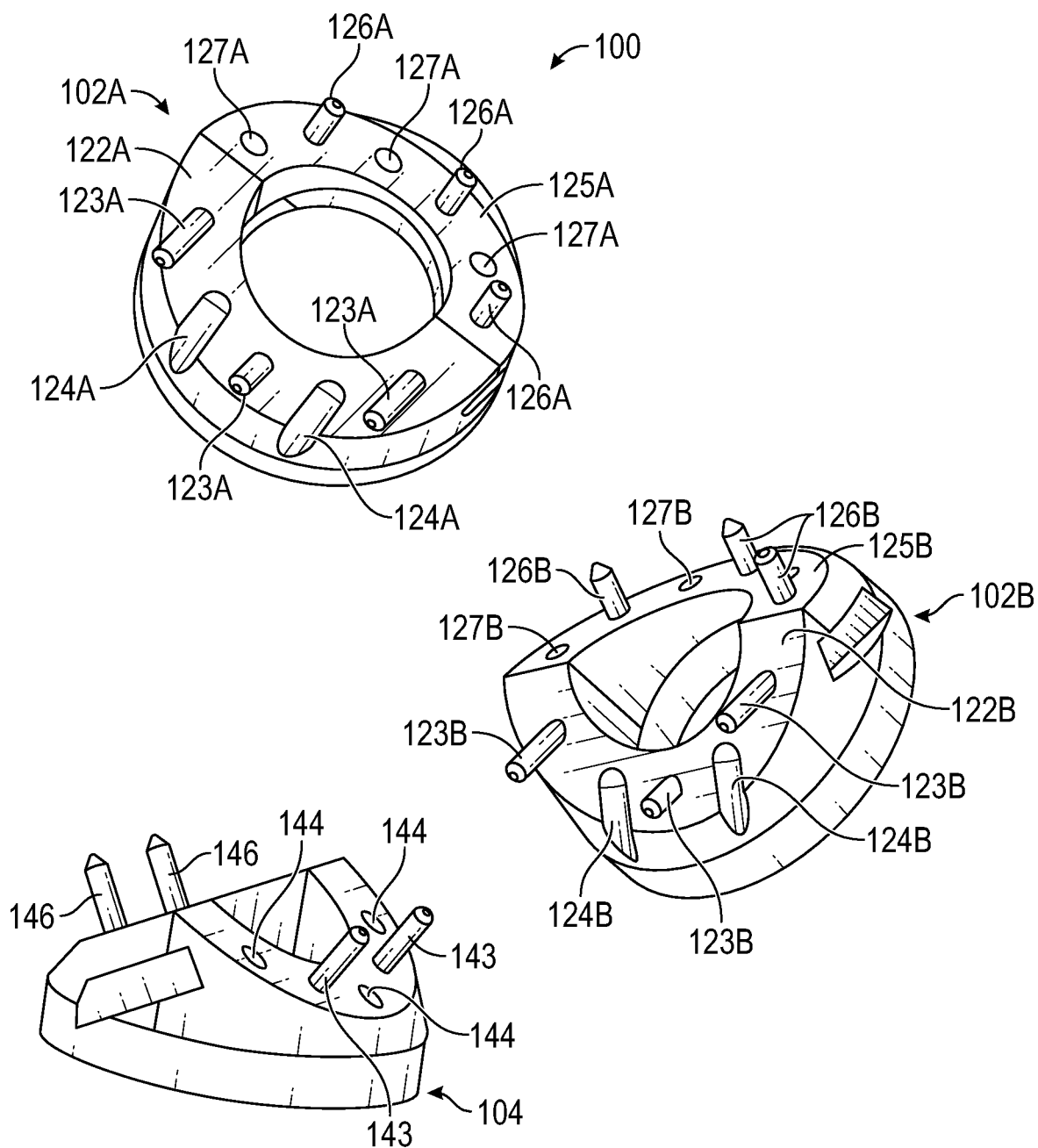
FIGS. 5A-5D are a series of illustrations showing engagement of the first receiving coupler ring, the second receiving coupler ring, and the donor ring of the multi-way coupler ring assembly of FIG. 1.
Figure 5B:
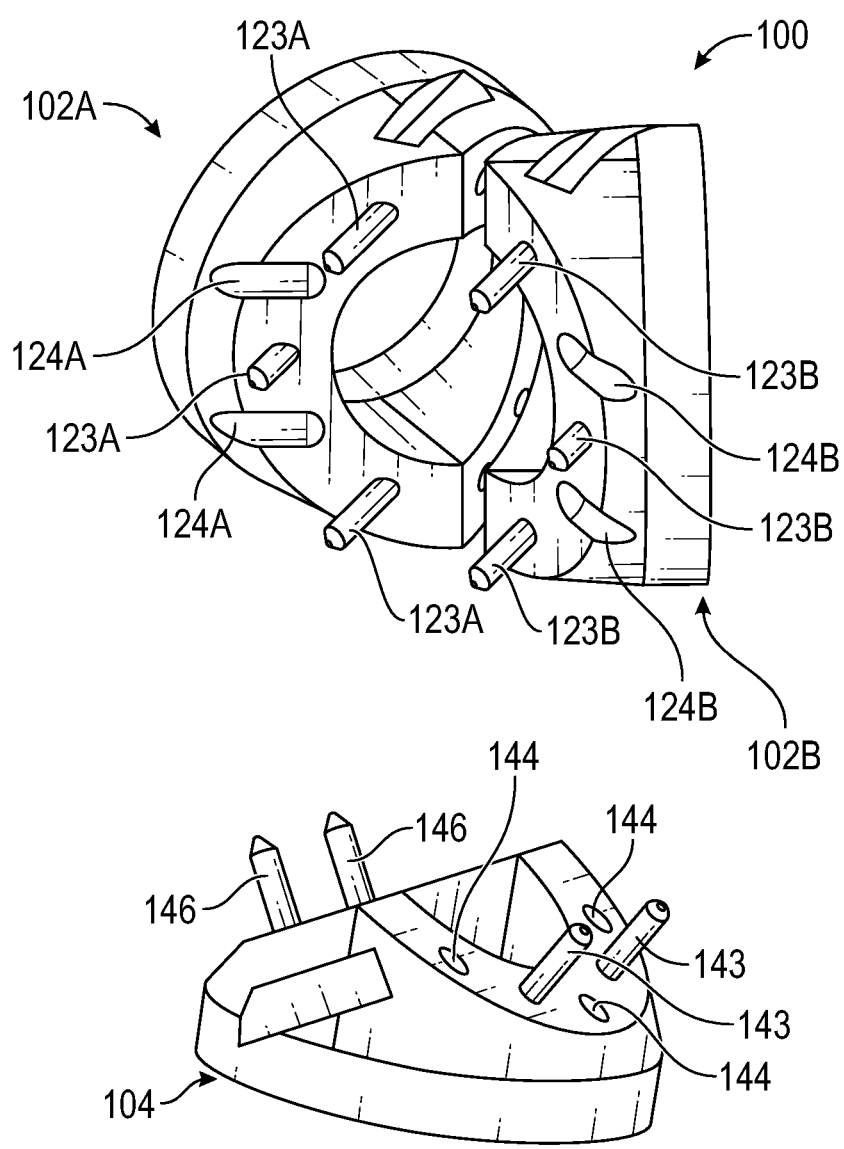
Figure 5C:
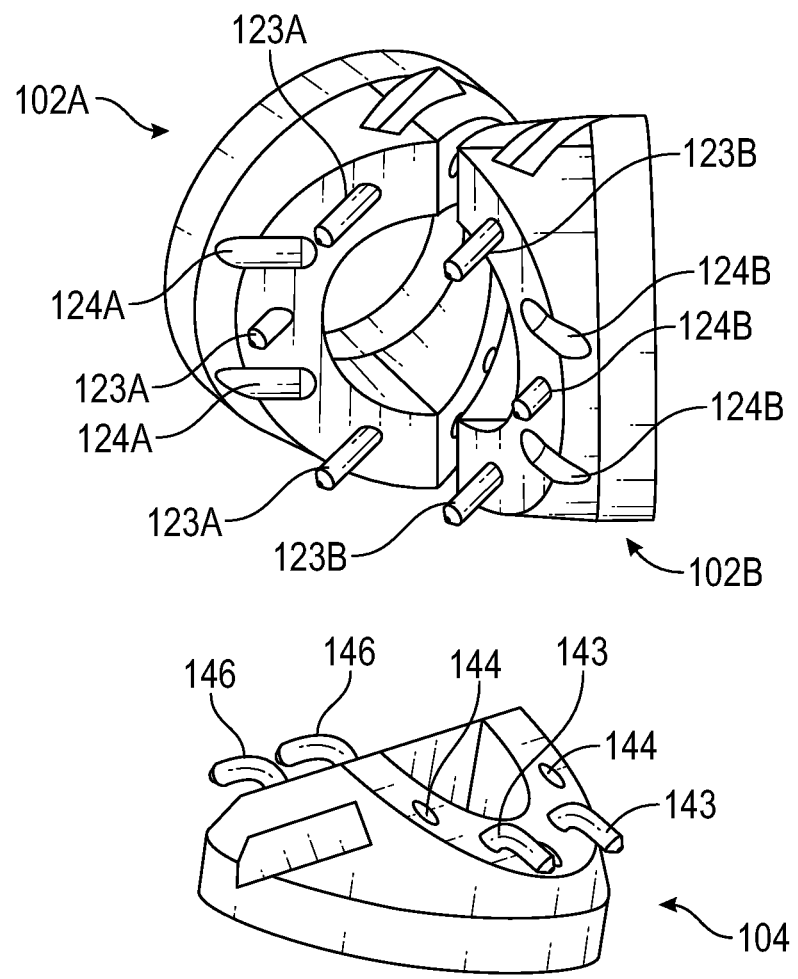
Figure 5D:
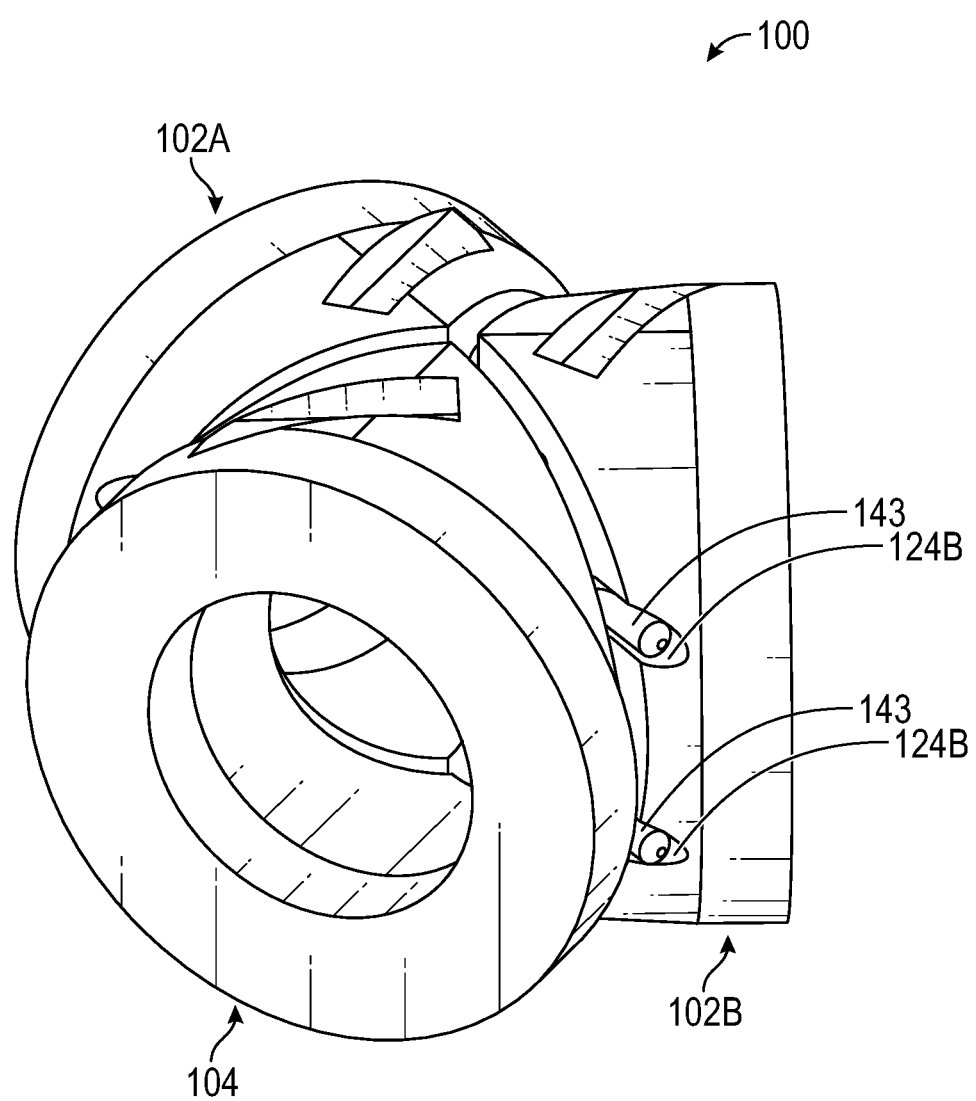

As shown in FIG. 3, the first plurality of pins 143 defined along the first face 142 of the donor coupler ring 104 can be oriented towards the second receiving coupler ring 102B and the second plurality of pins 146 defined along the second face 145 of the donor coupler ring 104 can be oriented towards the first receiving coupler ring 102A. In some embodiments, the first plurality of pins 143 extends perpendicularly from the first face 142 and the second plurality of pins 146 extends perpendicularly from the second face 145. Further, as shown in FIGS. 5B and 5C, the first and second pluralities of pins 143 and 146 are deformable and can be bent away from the channel 140. It should be noted that the first plurality of pin receptacles 124A of the first receiving coupler ring 102A and the first plurality of pin receptacles 124B of the second receiving coupler ring 102B define a notched configuration to receive the bent-away first and second pluralities of pins 143 and 146.

Likewise, the first and second faces 142 and 145 each include a plurality of pin receptacles 144 and 147. Specifically, the first face 142 includes a first plurality of pin receptacles 144 for engagement with the second receiving coupler ring 102B and the second face 145 includes a second plurality of pin receptacles 147 for engagement with the first receiving coupler ring 102B. In some embodiments, the first plurality of pin receptacles 144 defined along the first face 142 of the donor coupler ring 104 are configured to receive the second plurality of pins 127B of the second receiving coupler ring 102B. In some embodiments, to receive the second plurality of pins 127B of the second receiving coupler ring 102B, the first plurality of pin receptacles 144 are oriented along a direction of elongation of the channel 140. Similarly, the second plurality of pin receptacles 147 defined along the second face 145 of the donor coupler ring 104 are configured to receive the second plurality of pins 127A of the first receiving coupler ring 102A. To receive the second plurality of pins 127B of the second receiving coupler ring 102B, the first plurality of pin receptacles 144 are oriented along a direction of elongation of the channel 140.

Further, the donor coupler ring 104 defines a peripheral surface 152 that includes a pair of slots 153 for engagement with the coupler device 20 (FIG. 7A). The donor coupler ring 104 additionally includes a rear face 151 (FIG. 7E) defined opposite to the wedged face 141. In the embodiment shown, the wedged face 141 defines a second angle between the first face 142 and the second face 145, which is in some embodiments, may be a 120 degree angle; however, other angles are contemplated.

FIGS. 6-13 illustrate a coupler 10 for coupling the components of the multi-way coupler ring assembly 100 during an end-to-side anastomosis procedure. In some embodiments, the coupler 10 can be configured to access a receiving vessel and a donor vessel of a patient in a surgical corridor of approximately four centimeters below a tissue surface of the patient. In other embodiments, a device may be operable for gaining entry into a surgical corridor of more or less than four centimeters below the tissue surface. The coupler 10 can be employed by any surgeon familiar with microvascular anastomosis. The coupler 10 defines a carriage assembly 20 moveable within a body assembly 30. The carriage assembly 20 defines a first receiving arm 24A, a second receiving arm 24B, and a donor arm 25 that each respectively engage the first receiving coupler ring 102A, the second receiving coupler ring 102B and the donor coupler ring 104. In particular, the pair of arm slots 133A of the first receiving coupler ring 102A engage an open portion 44A of the first receiving arm 24A, the pair of arm slots 133B of the second receiving coupler ring 102B engage an open portion 44B of the second receiving arm 24B, and the pair of arm slots 153 of the donor coupler ring 104 engage an open portion 46 of the donor arm 25.

Figure 12C:
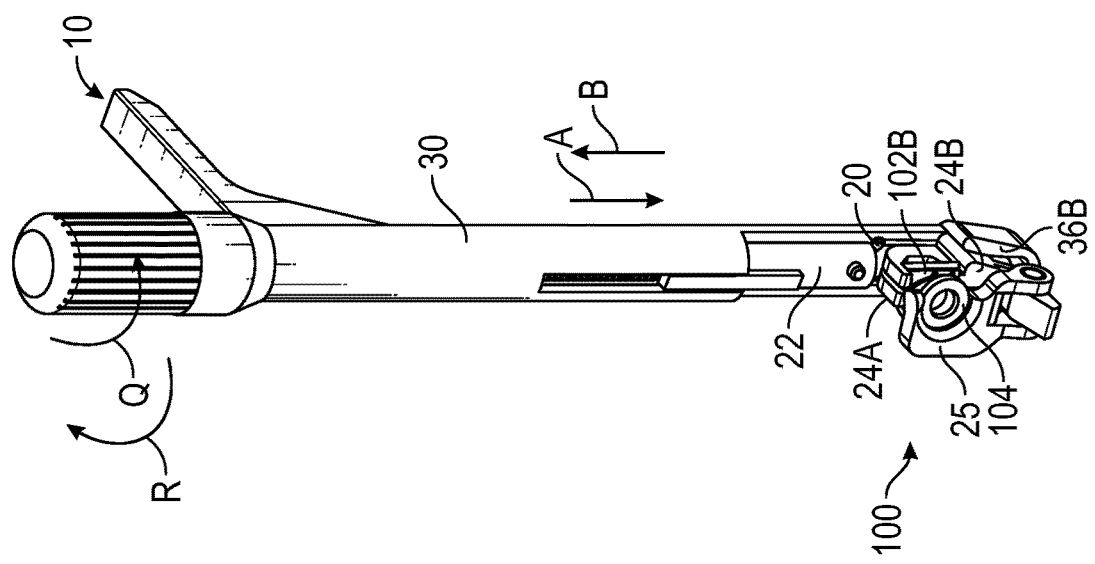
FIGS. 12A-12C are a series of illustrations showing engagement of the first receiving coupler ring, the second receiving coupler ring, and the donor ring of the multi-way coupler ring assembly of FIG. 1 through actuation of the coupler device of FIG. 6.
Figure 12B:
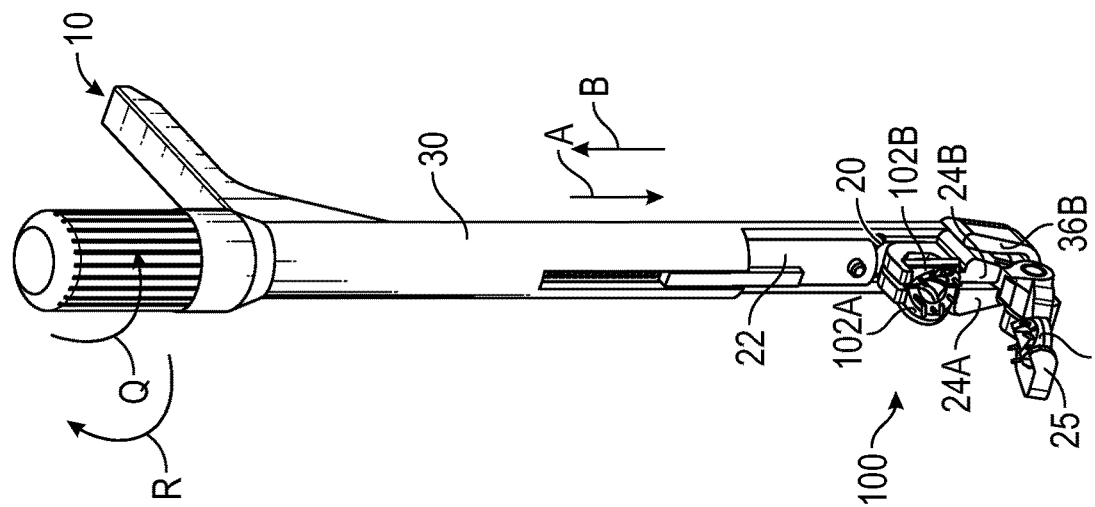
Figure 12A:
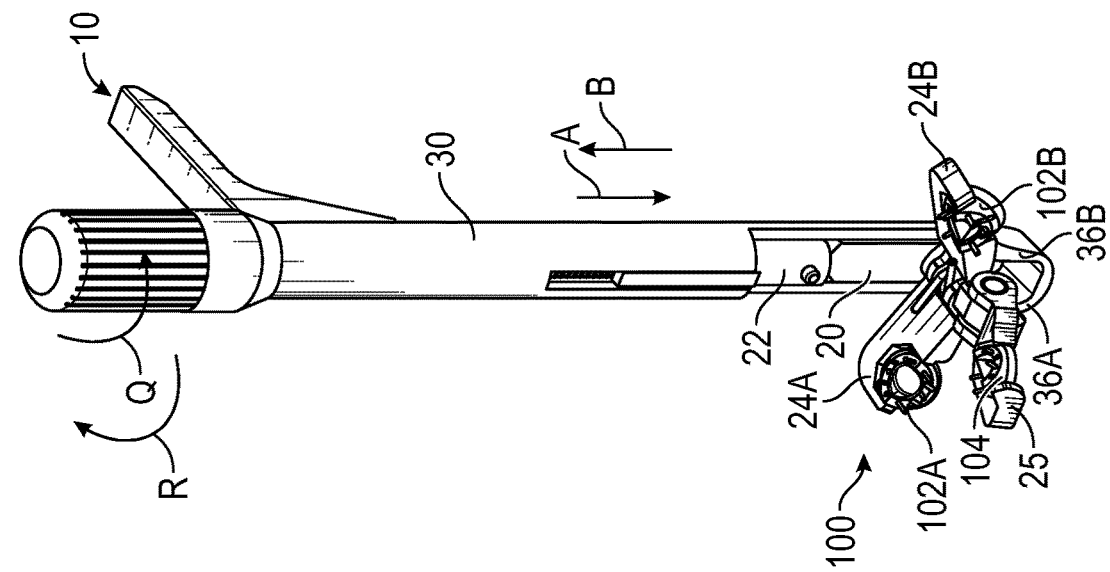

In some embodiments, the carriage assembly 20 is removables from the body assembly 30 and can be disposable. The carriage assembly 20 is moveable within a channel 33 of the body assembly 30 in a first axial direction A or an opposite second axial direction B (FIGS. 12A-12C). The body assembly 30 includes a rod 32 in association with a shuttle 22 and a carriage 21 of the carriage assembly 20 configured to actuate the entire carriage assembly 20 in the first or opposite second axial direction A or B. As shown in FIGS. 7A-C and 12A, in a default state of the carriage assembly 20, the first receiving arm 24A and the second receiving arm 24B assume an open position. In some embodiments, the open position is maintained by a spring 28 that biases the first receiving arm 24A and the second receiving arm 24B. Actuating the carriage assembly 20 in the first axial direction A causes the first receiving arm 24A and the second receiving arm 24B to assume a closed configuration. In particular, the body assembly 30 defines a first wedge 36A and a second wedge 36B at an open portion 34 of the body assembly 30. As the carriage assembly 20 is actuated in the first axial direction A, the first receiving arm 24A and the second receiving arm 24B are forced into the closed position of FIGS. 7D and 12B by the first and second wedges 36A and 36B. As illustrated, this action couples the first receiving coupler ring 102A to the second receiving coupler ring 102B.

As illustrated directly in FIGS. 7D, 7E, 12B and 12C, the donor arm 25 of the carriage assembly 20 is configured for actuation along a plane perpendicular to the first receiving arm 24A and the second receiving arm 24B to couple the donor coupler ring 104 with the first receiving coupler ring 102A and the second receiving coupler ring 102B. In some embodiments, as shown in the exploded view of FIG. 9, the carriage assembly 20 includes a primary pin 26 defined perpendicular to the carriage 21 and shuttle 22 that captures the first receiving arm 24A and the second receiving arm 24B against the carriage 21, and additionally provides an engagement point for a secondary pin 27. The secondary pin 27 directly couples the donor arm 25 to the primary pin 26 and provides an axis of rotation for the donor arm 25 when actuating the donor arm 25 between an open position (shown in FIG. 12B) and a closed position (shown in FIG. 12C). Actuation of the donor arm 25 to the closed position results in coupling the donor coupler ring 104 to the first receiving coupler ring 102A and the second receiving coupler ring 102B.

Figure 9:
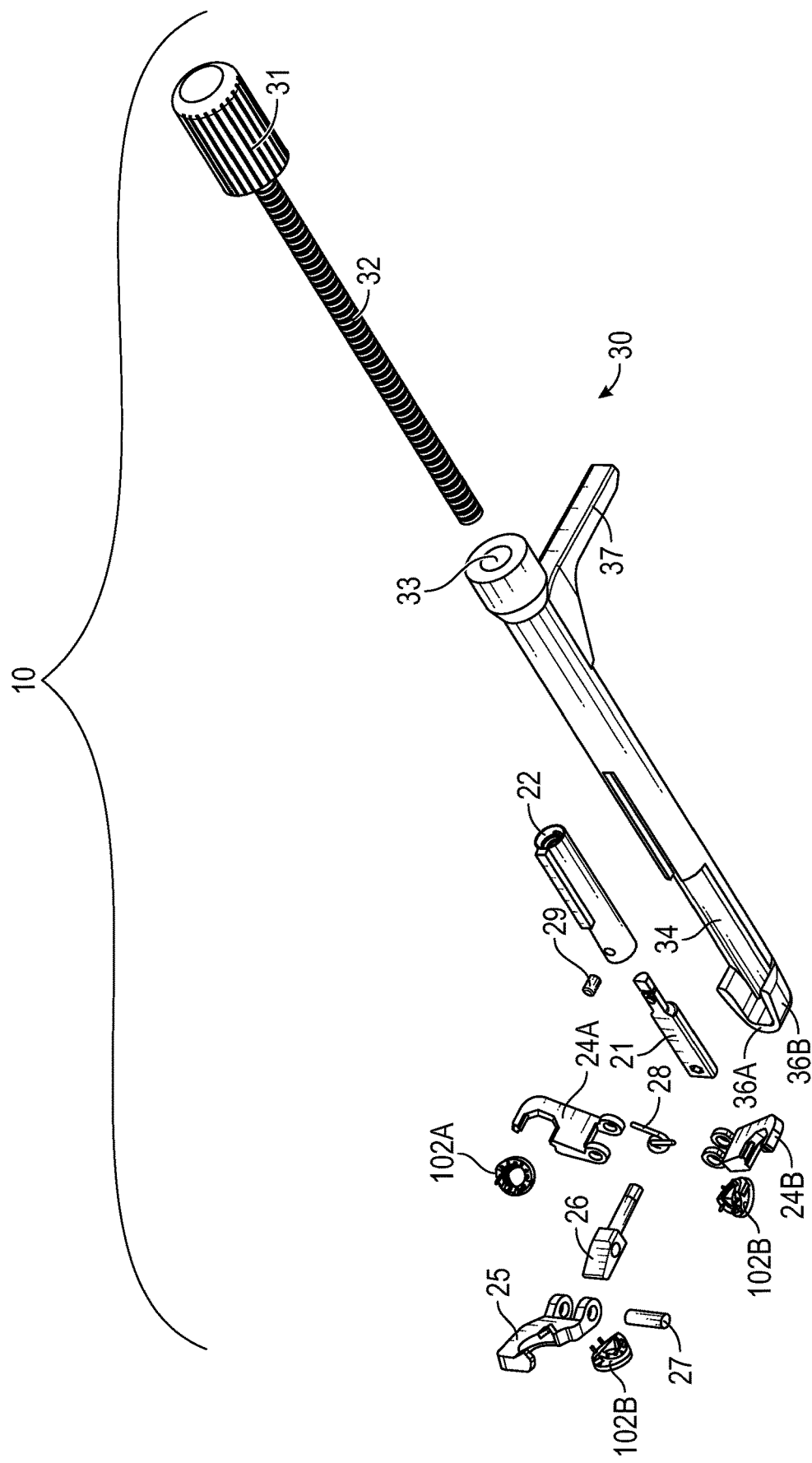
FIG. 9 is an illustration showing an exploded view of a coupler device for coupling the multi-way coupler ring assembly of FIG. 1.
Figure 10:
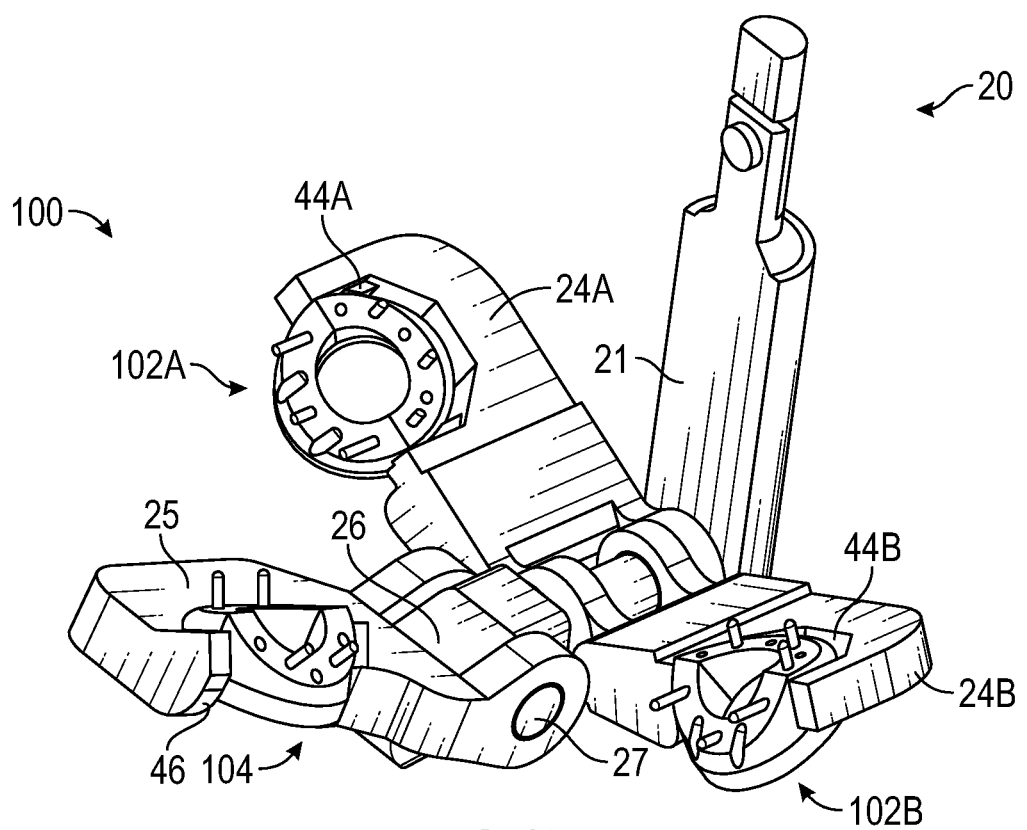
FIG. 10 is an illustration showing the carriage assembly of FIG. 8 engaged with the multi-way coupler ring assembly of FIG. 1.
Figure 11:
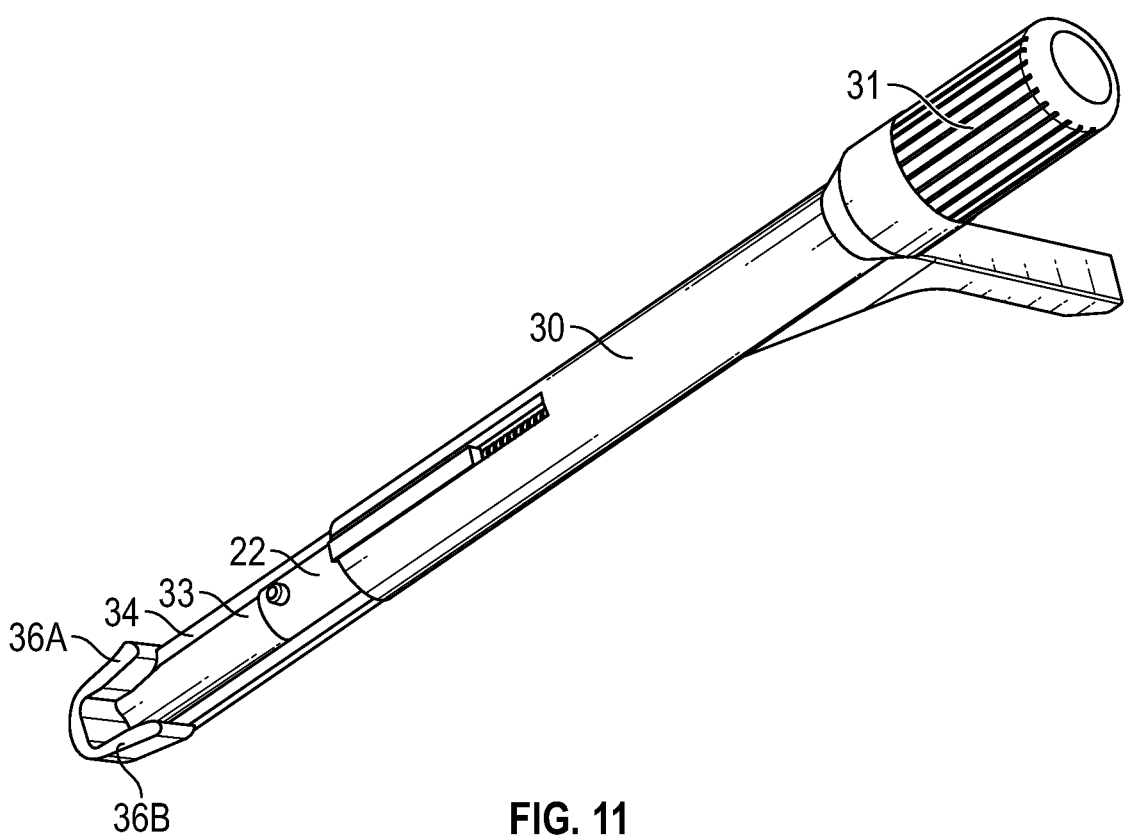
FIG. 11 is an illustration showing the body assembly of FIG. 8.

In some embodiments, the body assembly 30 includes a knob 31 or other actuating means in association with the rod 32 for actuating the carriage assembly 20 in the first or opposite second axial direction A or B. In the embodiment of FIG. 9, the rod 32 defines a threaded surface and the shuttle 22 of the carriage assembly 20 includes a threaded channel 23 configured for engagement with the threaded surface of the rod 32 such that as the rod 32 is rotated in a first rotational direction Q or an opposite second rotational direction R (FIGS. 12A-12C), the carriage assembly 20 is consequently actuated in the first axial direction A or the opposite second axial direction B within the channel 33 of the body assembly 30. In some embodiments, the donor arm 25 is manually rotated to the closed position using forceps.

Figure 13:
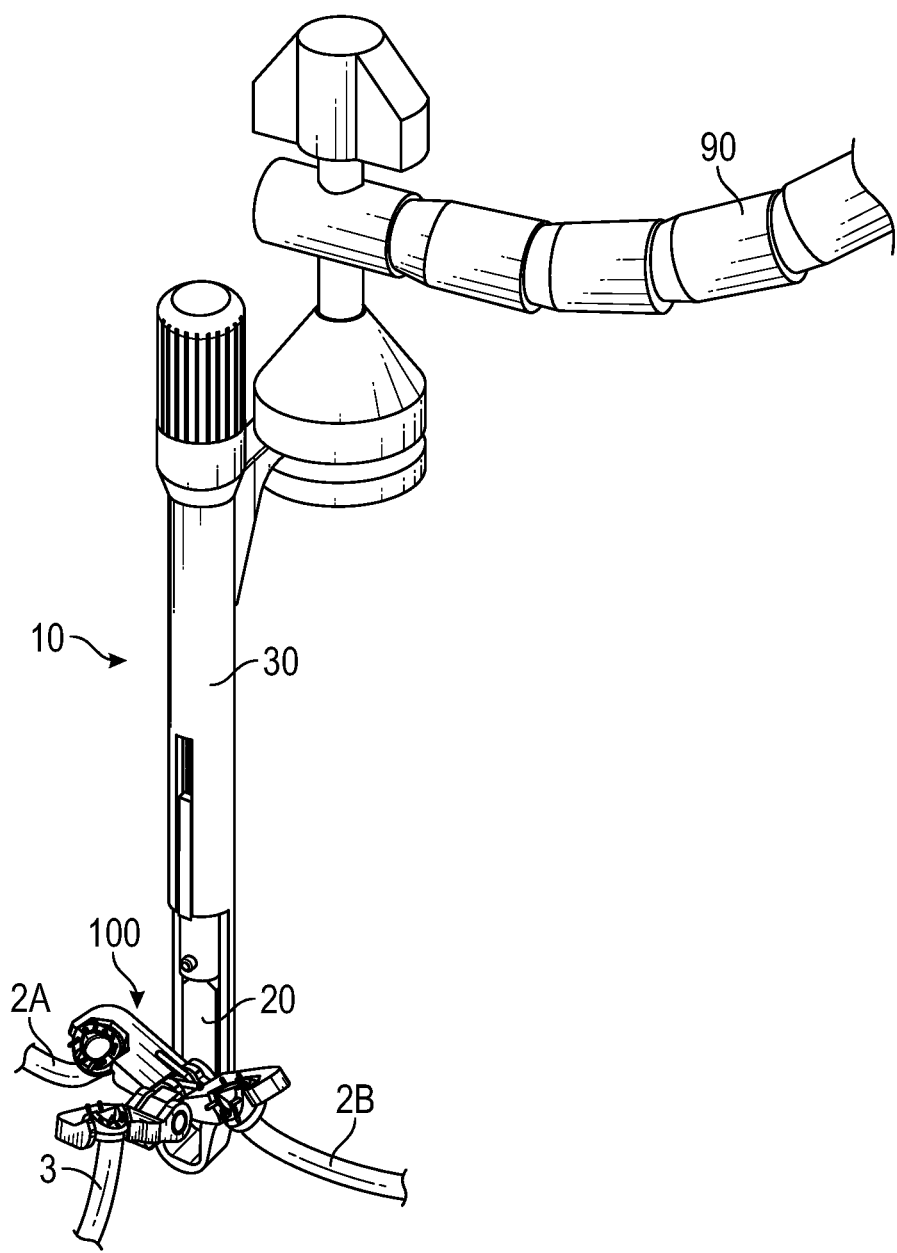
FIG. 13 is an illustration showing engagement of the coupler device of FIG. 6 with a retractor device.
Figure 14:
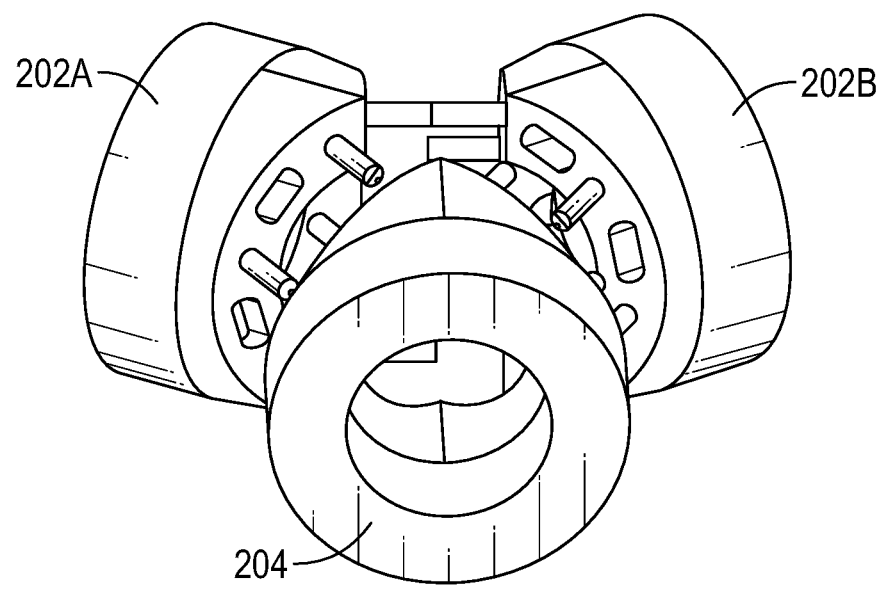
FIG. 14 is a is an illustration showing a second embodiment of a multi-way coupler ring assembly.
Figure 15:
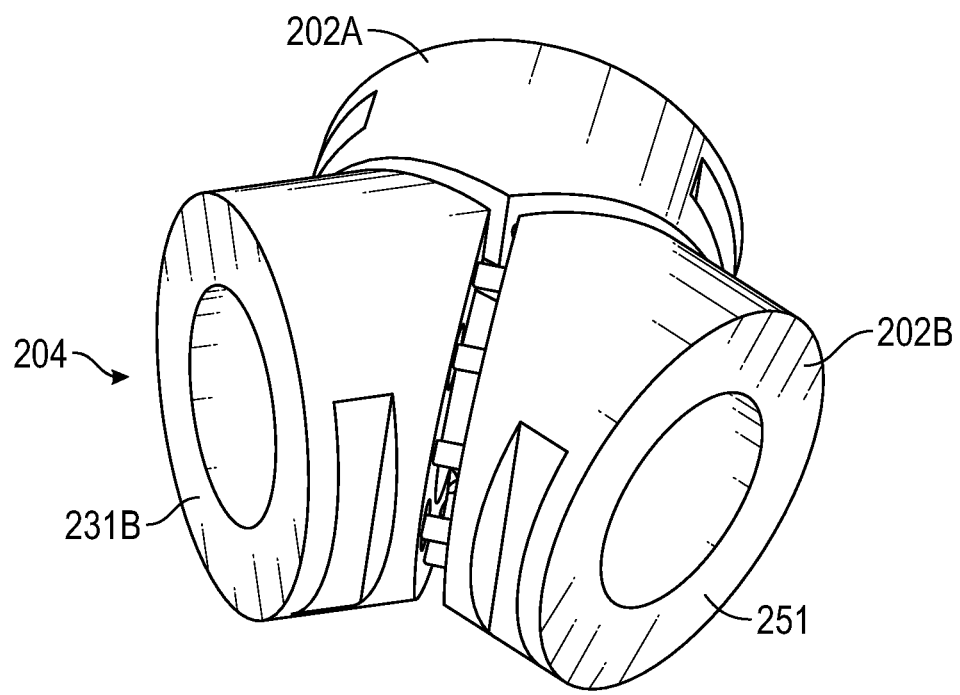
FIG. 15 is an illustration showing the multi-way coupler ring assembly of FIG. 14 in a coupled position.

FIG. 13 illustrates engagement of the coupler 10 with a retractor 90. In some embodiments, the body assembly 30 includes a stabilizer flange 37 that is configured to be grasped by retractor 90 and can additionally provide an element for grasping by a practitioner.

FIGS. 5A-5D and 7A-7E illustrate a method of joining the first receiving vessel 2A and the second receiving vessel 2B in a three-way connection with the donor vessel 3 using the multi-way coupler ring assembly 100. FIGS. 5A-5D particularly illustrate coupling components of the multi-way coupler ring assembly 100 and FIGS. 7A-7E illustrate coupling components of the multi-way coupler ring assembly 100 with additional context including everted vessels and the coupler device 10. In some embodiments, the multi-way coupler ring assembly 100 is coupled in a stepwise manner; the first receiving coupler ring 102A is first coupled with the second receiving coupler ring 102B and the donor coupler ring 104 is subsequently coupled with the first and second receiving coupler rings 102A and 102B. In other embodiments discussed further herein, components of the multi-way coupler ring assembly can be coupled simultaneously.

Figure 7B:
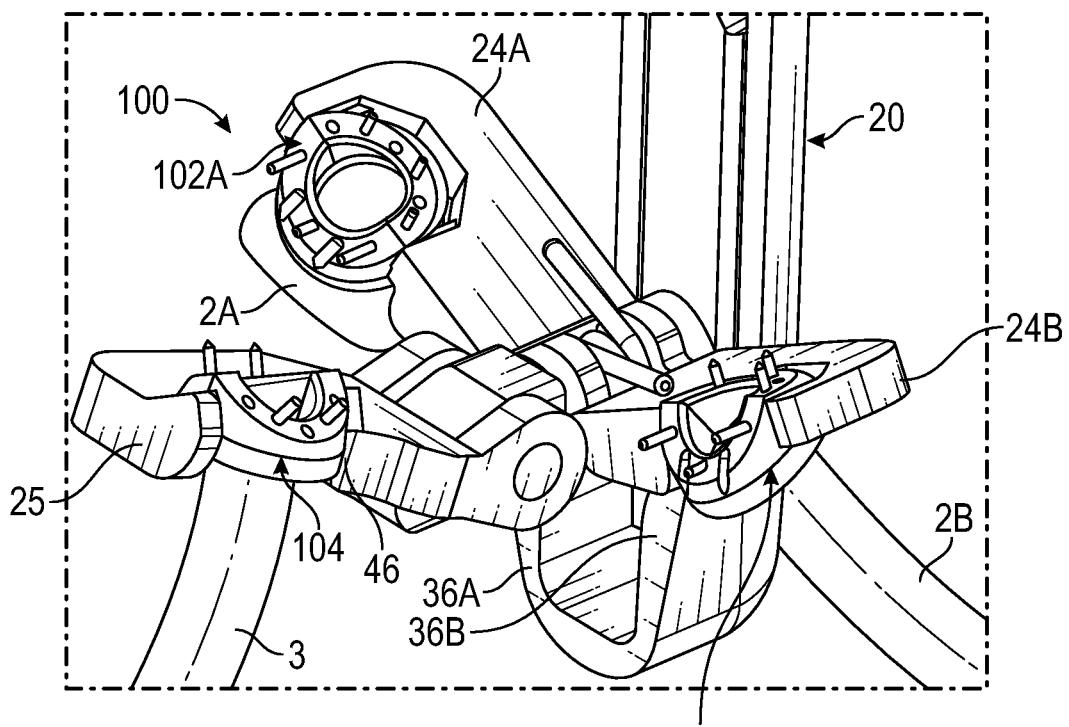
Figure 7C:
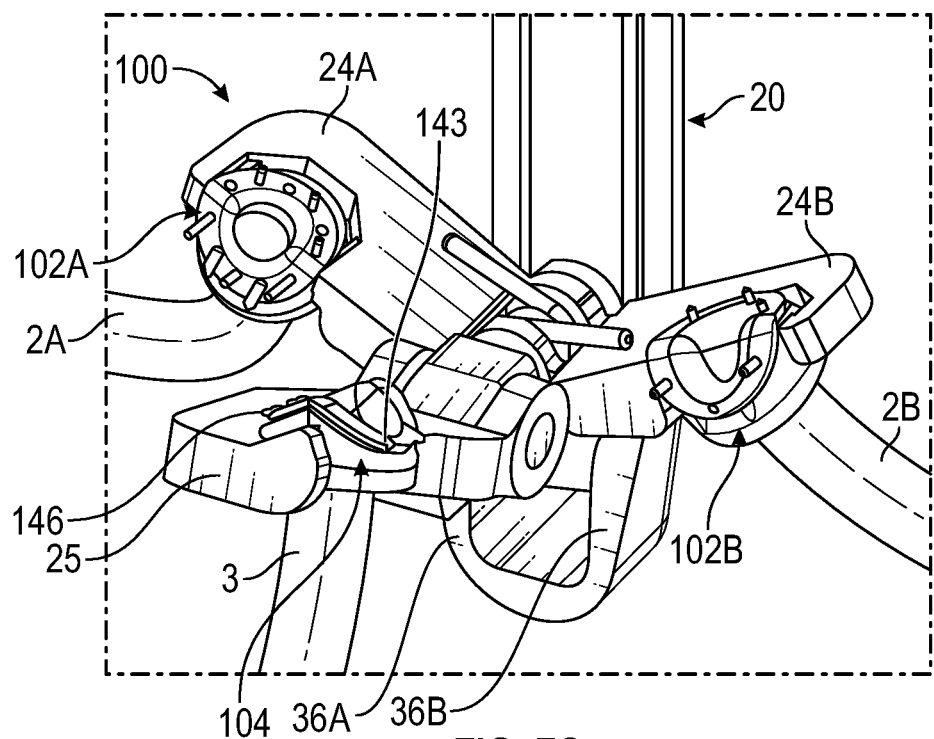

As illustrated in FIGS. 7A-7C, the first receiving coupler ring 102A engages within the first receiving arm 24A of the coupler device 10, the second receiving coupler ring 102B engages within the second receiving arm 24B of the coupler device 10 and the donor coupler ring 104 engages within the donor arm 25 of the coupler device 10.

The receiving vessel is initially severed into a first receiving vessel 2A and a second receiving vessel 2B. The first receiving vessel 2A is inserted through the channel 120A through the rear face (not shown) of the first coupler ring 102A and is everted onto the first and second pluralities of pins 123A and 126A of the first coupler ring 102A. Similarly, the second receiving vessel 2B is inserted through the channel 120B through the rear face (not shown) of the second coupler ring 102B and is everted onto the first and second pluralities of pins 123B and 126B of the second coupler ring 102B.

The donor coupler ring 104 receives the donor vessel 3 through the channel 140 through the rear face 151 (FIG. 7E) of the donor coupler ring 104 and is everted onto the first and second pluralities of pins 143B and 146B of the donor coupler ring 104. In some embodiments, the first and second pluralities of pins 143B and 146B of the donor coupler ring 104 are then bent away from the channel 140; however, in other embodiments the first and second pluralities of pins 143B and 146B can be pre-bent and can be bent before or after engagement of the first coupler ring 102A with the second coupler ring 102B.

Figure 7D:
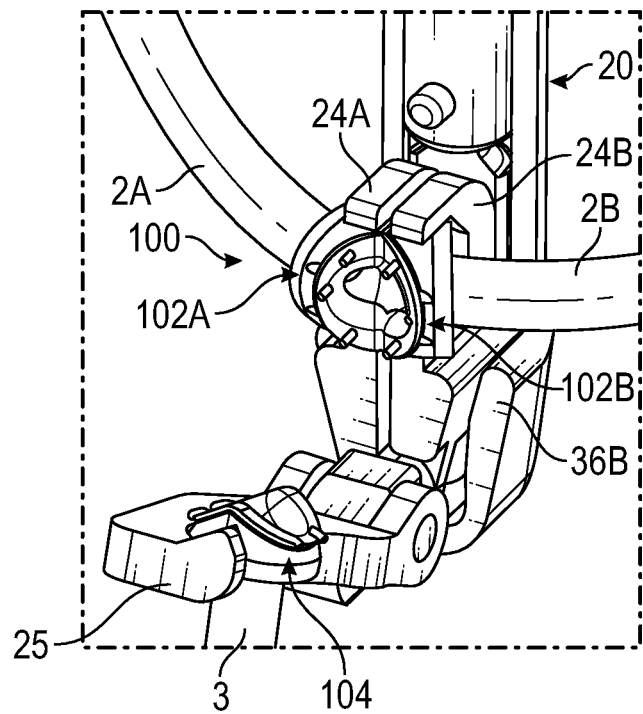
Figure 7E:
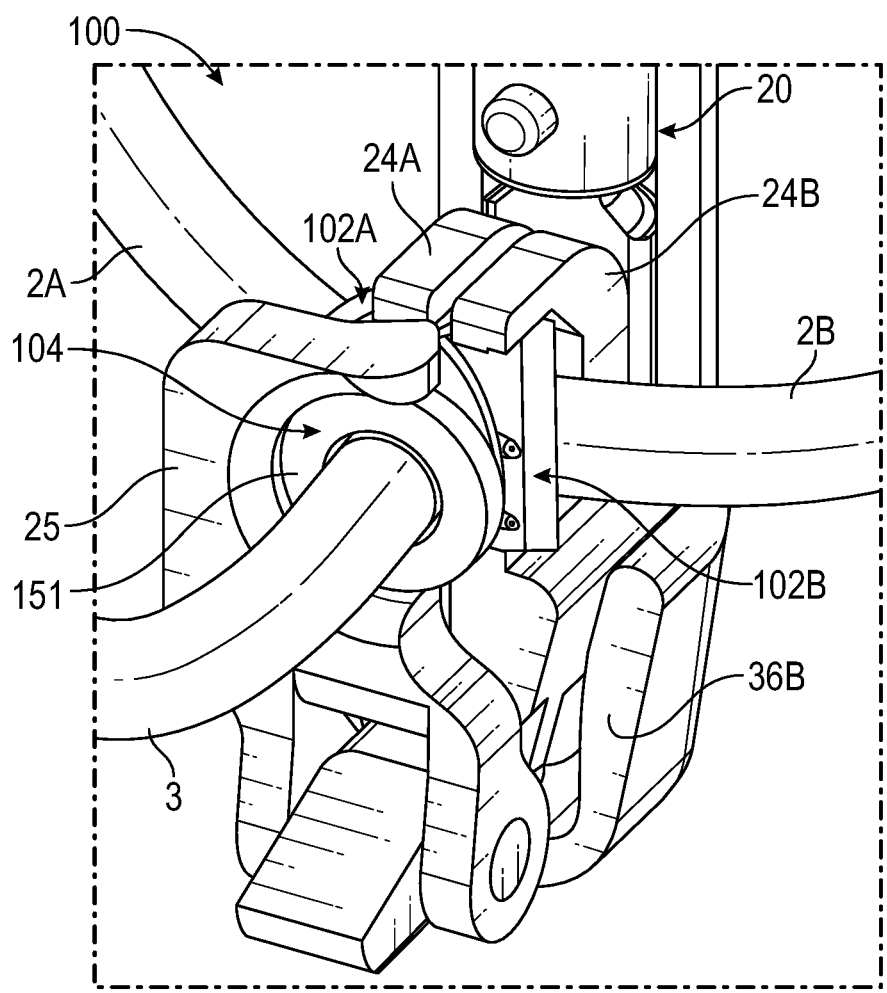
Figure 8:
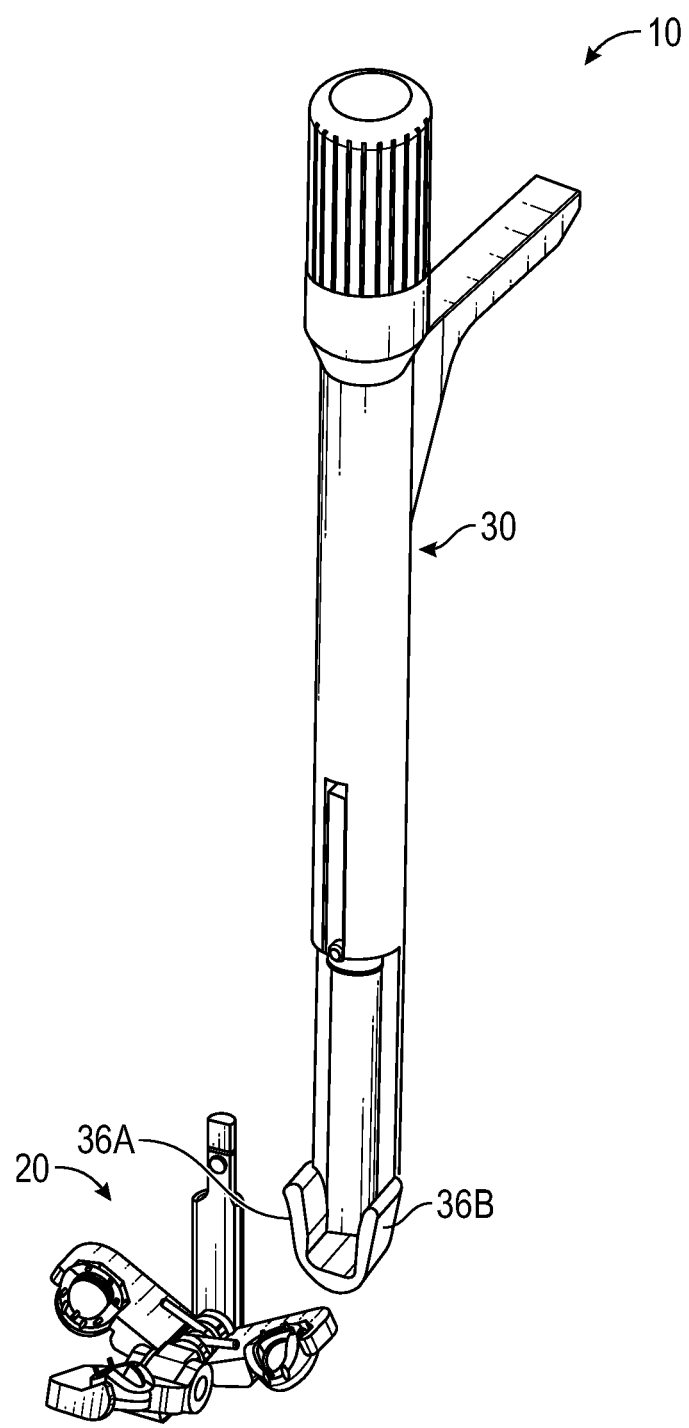
FIG. 8 is an illustration showing a perspective view of a coupler device for coupling the multi-way coupler ring assembly of FIG. 1 with a carriage assembly removed from a body assembly of the coupler device of FIG. 6.

As shown in FIGS. 5A, 5B, 7C and 7D, the first receiving coupler ring 102A engages the second receiving coupler ring 102B. In particular, the second face 125A of the first receiving coupler ring 102A engages the second face 125B of the second receiving coupler ring 102B as shown in FIGS. 5B and 7D. The second plurality of pins 126A of the first receiving coupler ring 102A are inserted into the second plurality of pin receptacles 127B of the second receiving coupler ring 102B and the second plurality of pins 126B of the second receiving coupler ring 102B are inserted into the second plurality of pin receptacles 127A of the first receiving coupler ring 102A. In some embodiments, this is achieved using the coupler 10; in particular, the first receiving arm 24A that holds the first receiving coupler ring 102A and the second receiving arm 24B that holds the second receiving coupler ring 102B are actuated into the closed position by the carriage assembly 20 of the coupler 10.

As shown in FIGS. 5C, 5D, 7D and 7E, the donor coupler ring 104 is coupled with the first receiving coupler ring 102A and the second receiving coupler ring 102B. In particular, the first face 142 of the donor coupler ring 104 engages the first face 122B of the second receiving coupler ring 102B and the second face 145 of the donor coupler ring 104 engages the first face 122A of the first receiving coupler ring 102A as shown in FIGS. 5B and 7D. The first plurality of pins 143 of the donor coupler ring 104 are inserted into the first plurality of pin receptacles 124B of the second receiving coupler ring 102B and the second plurality of pins 146 of the donor coupler ring 104 are inserted into the first plurality of pin receptacles 124A of the first receiving coupler ring 102A. Additionally, the first plurality of pins 123A of the first receiving coupler ring 102A are inserted into the second plurality of pin receptacles 147 of the donor coupler ring 104 and the first plurality of pins 123B of the second receiving coupler ring 102B are inserted into the first plurality of pin receptacles 144 of the donor coupler ring 104. In some embodiments, this is achieved using the coupler 10; in particular, the donor arm 25 that holds the donor coupler ring 104 can be guided into the closed position by the carriage assembly 20 of the coupler 10. Following coupling of the first receiving coupler ring 102A, the second receiving coupler ring 102B, and the donor coupler ring 104, the coupler device 10 can be removed.

FIGS. 14-17B illustrate a second embodiment of the multi-way coupler ring assembly 200 and a coupler device 50 configured to couple together components of the multi-way coupler ring assembly 200. The multi-way coupler ring assembly 200 enables end-to-side anastomosis through severing a receiving vessel to form a first receiving vessel and a second receiving vessel that are joined in a three-way connection with the donor vessel using the multi-way coupler ring assembly 200. In particular, the multi-way coupler ring assembly 200 is configured to simultaneously couple a first end of a receiving vessel with a second end of the receiving vessel and the donor vessel in a three-way junction. The multi-way coupler ring assembly 200 includes a first receiving coupler ring 202A configured to receive a first receiving vessel and a second receiving coupler ring 202B configured to receive a second receiving vessel and couple with the first receiving coupler ring 202A. The multi-way coupler ring assembly 200 further includes a donor coupler ring 204 configured to receive the donor vessel and simultaneously couple with the first receiving coupler ring 202A and the second receiving coupler ring 202B. The first receiving coupler ring 202A, the second receiving coupler ring 202B and the donor coupler ring 204 each respectively define a wedged face to enable three-way simultaneous or stepwise coupling with one another. In contrast with the previous embodiment of the multi-way coupler ring assembly 100 (FIGS. 1-7E) in which the donor coupler ring 104 is not interchangeable with the first and second receiving coupler rings 102A and 102B, the first receiving coupler ring 202A, the second receiving coupler ring 202B and the donor coupler ring 204 of the multi-way coupler ring assembly 200 can be identical and/or interchangeable.

Figure 16A:
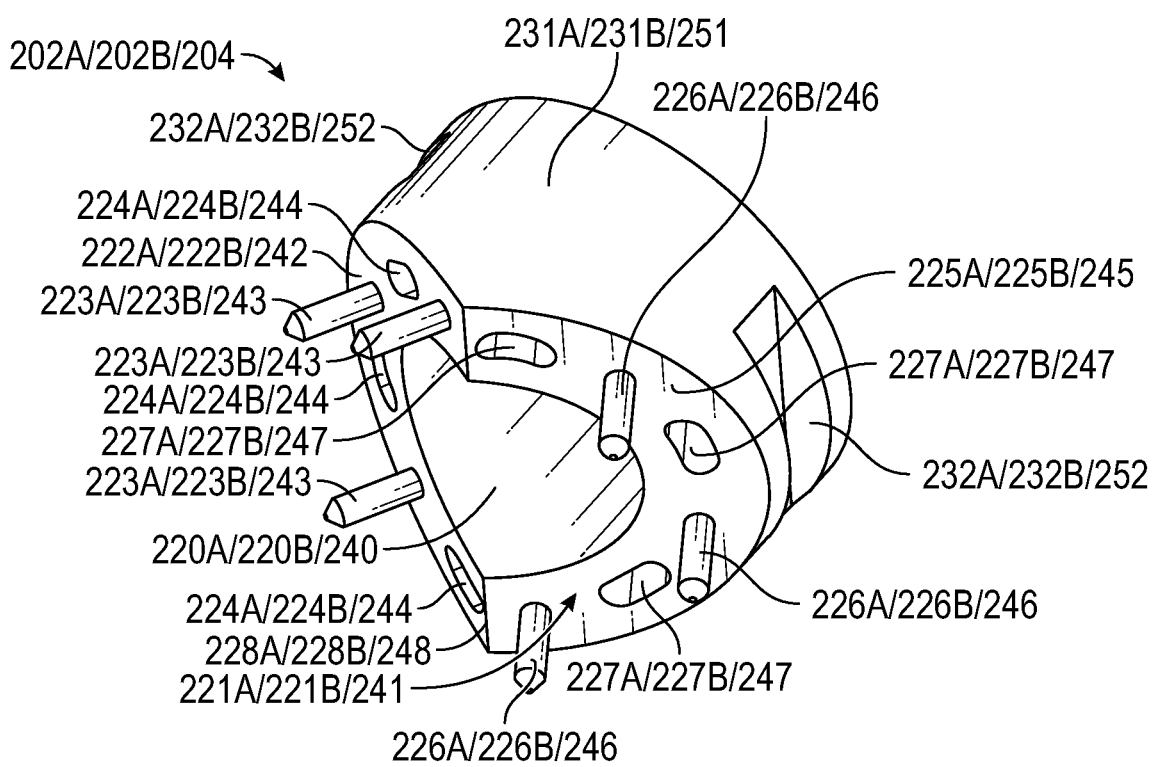
FIGS. 16A and 16B are respective perspective and front illustrations showing a first receiving coupler ring, a second receiving coupler ring or a donor coupler ring of the multi-way coupler ring assembly of FIG. 14.
Figure 16B:
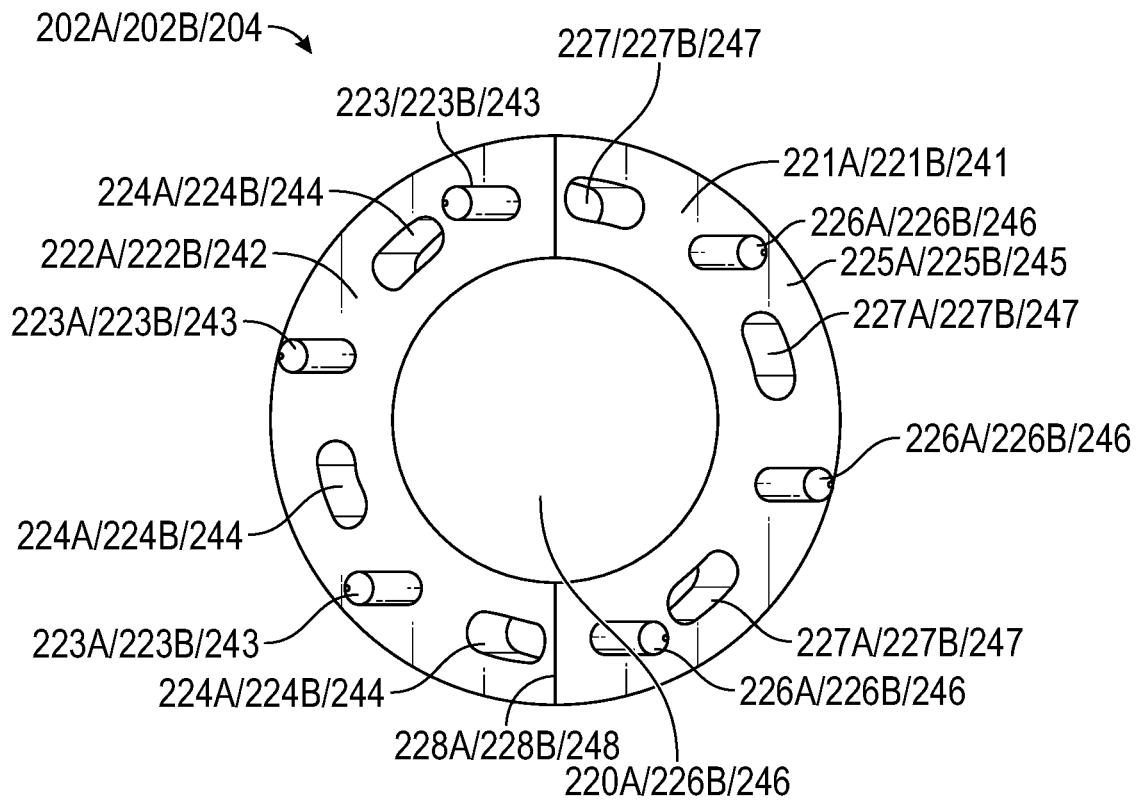

FIGS. 16A and 16B, show a component of the multi-way coupler ring assembly 200 which can embody the first receiving coupler ring 202A, the second receiving coupler ring 202B or the donor coupler ring 204; FIGS. 16A and 16B are annotated in terms of the first receiving coupler ring 202A, the second receiving coupler ring 202B and the donor coupler ring 204. The first receiving coupler ring 202A (second receiving coupler ring 202B/donor coupler ring 204) is generally ring-shaped and defines a wedged face 221A (221B/241) for engagement with the remaining coupler rings 202B and 204 (202A and 204/202A and 202B), and additionally includes a channel 220A (220B/240) for passage of a first receiving vessel (second receiving vessel/donor vessel). As shown, the channel 220A (220B/240) of the first receiving coupler ring 202A (second receiving coupler ring 202B/donor coupler ring 204) defines an elliptical cross-section to reduce an eversion distance required of the first receiving vessel. The wedged face 221A (221B/241) defines a first face 222A (222B/242) and an opposite second face 225A (225B/245) divided by an apex 228A (228B/248) that enables three-way engagement with the remaining coupler rings 202B and 204 (202A and 204/202A and 202B).

The first and second faces 222A (222B/242) and 225A (225B/245) of the first receiving coupler ring 202A (second receiving coupler ring 202B/donor coupler ring 204) each include a respective first and second plurality of pins 223A (223B/243) and 226A (226B/246); in particular, the first face 222A of the first receiving coupler ring 202A includes the first plurality of pins 223A for engagement with the donor coupler ring 204 and the second face 225A includes a second plurality of pins 226A for engagement with the second receiving coupler ring 202B. Similarly, the first face 222B of the second receiving coupler ring 202B includes the first plurality of pins 223B for engagement with the donor coupler ring 204 and the second face 225B includes a second plurality of pins 226B for engagement with the first receiving coupler ring 202A. For the donor coupler ring 204, the first face 242 includes the first plurality of pins 243 for engagement with the second receiving coupler ring 202B and the second face 245 includes a second plurality of pins 246 for engagement with the first receiving coupler ring 202A.

As shown in FIG. 16A, the first plurality of pins 223A (223B/243) defined along the first face 222A (222B/242) of the first receiving coupler ring 202A (second receiving coupler ring 202B/donor coupler ring 204) are defined perpendicular to the first face 222A (222B/242). In contrast, the second plurality of pins 223A (223B/243) defined along the second face 225A (225B/245) of the first receiving coupler ring 202A (second receiving coupler ring 202B/donor coupler ring 204) are oriented perpendicular to the second face 225A (225B/245) of the first receiving coupler ring 202A (second receiving coupler ring 202B/donor coupler ring 204) as further shown in FIG. 16A. Additionally, the first and second plurality of pins 223A (223B/243) and 226A (226B/246) are also configured to capture an everted portion of the first receiving vessel (second receiving vessel/donor vessel). In the embodiment shown, the first and second plurality of pins 223A (223B/243) and 226A (226B/246) are deformable.

Likewise, the first and second faces 222A (222B/242) and 225A (225B/245) each include a respective first and second plurality of pin receptacles 224A (224B/244) and 227A (227B/247); in particular, the first face 222A of the first receiving coupler ring 202A includes the first plurality of pin receptacles 224A for engagement with the second plurality of pins 246 of the donor coupler ring 204 and the second face 225A includes a second plurality of pin receptacles 227A for engagement with the second plurality of pins 226B of the second receiving coupler ring 202B. Similarly, the first face 222B of the second receiving coupler ring 202B includes the first plurality of pin receptacles 224B for engagement with the first plurality of pins 243 of the donor coupler ring 204 and the second face 225B includes a second plurality of pin receptacles 227B for engagement with the second plurality of pins 226A of the first receiving coupler ring 202A. For the donor coupler ring 204, the first face 242 includes the first plurality of pin receptacles 244 for engagement with the first plurality of pins 223B of the second receiving coupler ring 202B and the second face 245 includes a second plurality of pin receptacles 247 for engagement with the first plurality of pins 226A of the first receiving coupler ring 202A.

The first plurality of pin receptacles 224A (224B/244) defined along the first face 222A (222B/242) and the second plurality of pin receptacles 227A (227B/247) defined along the second face 225A (225B/245) of the first receiving coupler ring 202A (second receiving coupler ring 202B/donor coupler ring 204) are each oriented perpendicular to their respective first and second faces 222A (222B/242) and 225A (225B/245) of the first receiving coupler ring 202A (second receiving coupler ring 202B/donor coupler ring 204) as further shown in FIG. 16A. In the embodiment shown, the first and second plurality of pin receptacles 224A (224B/244) and 227A (227B/247) are elliptical to aid with the first and second plurality of pins 223A (223B/243) and 226A (226B/246).

Figure 17A:
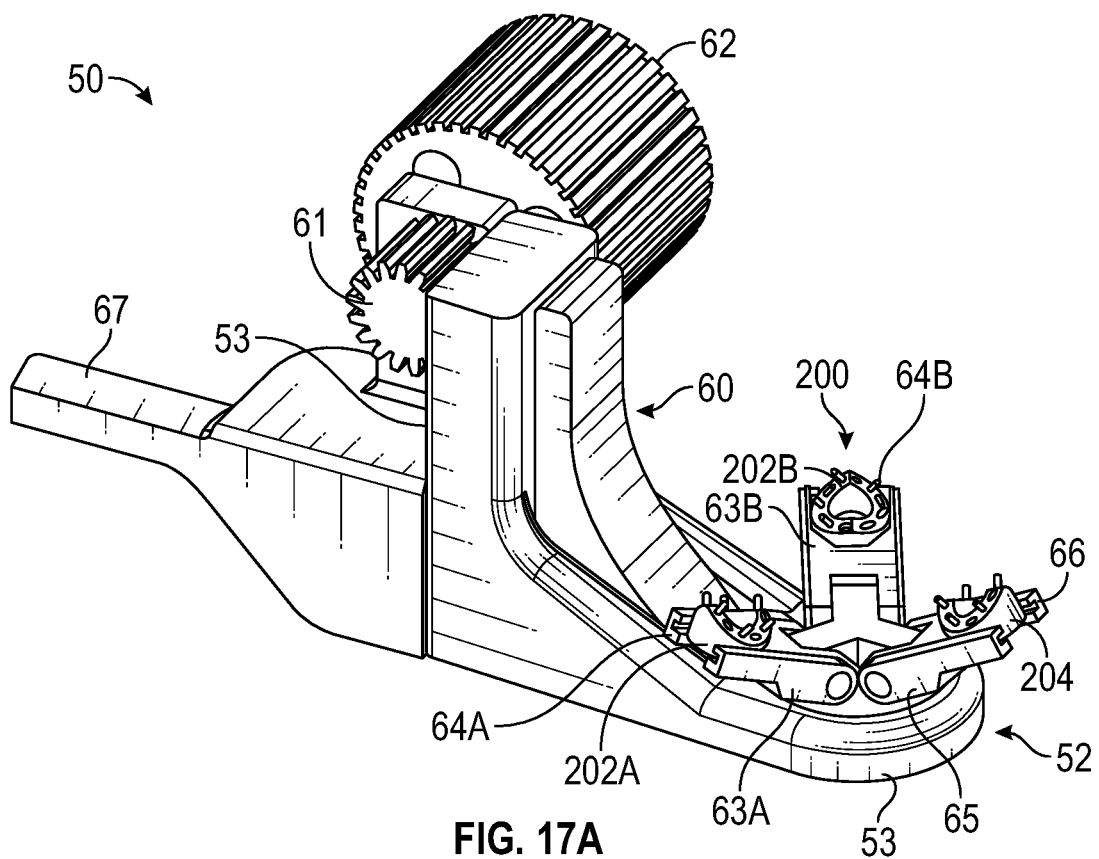
FIGS. 17A and 17B are respective illustrations showing a coupler device for coupling the multi-way coupler ring assembly of FIG. 14 in an open and closed position.
Figure 17B:
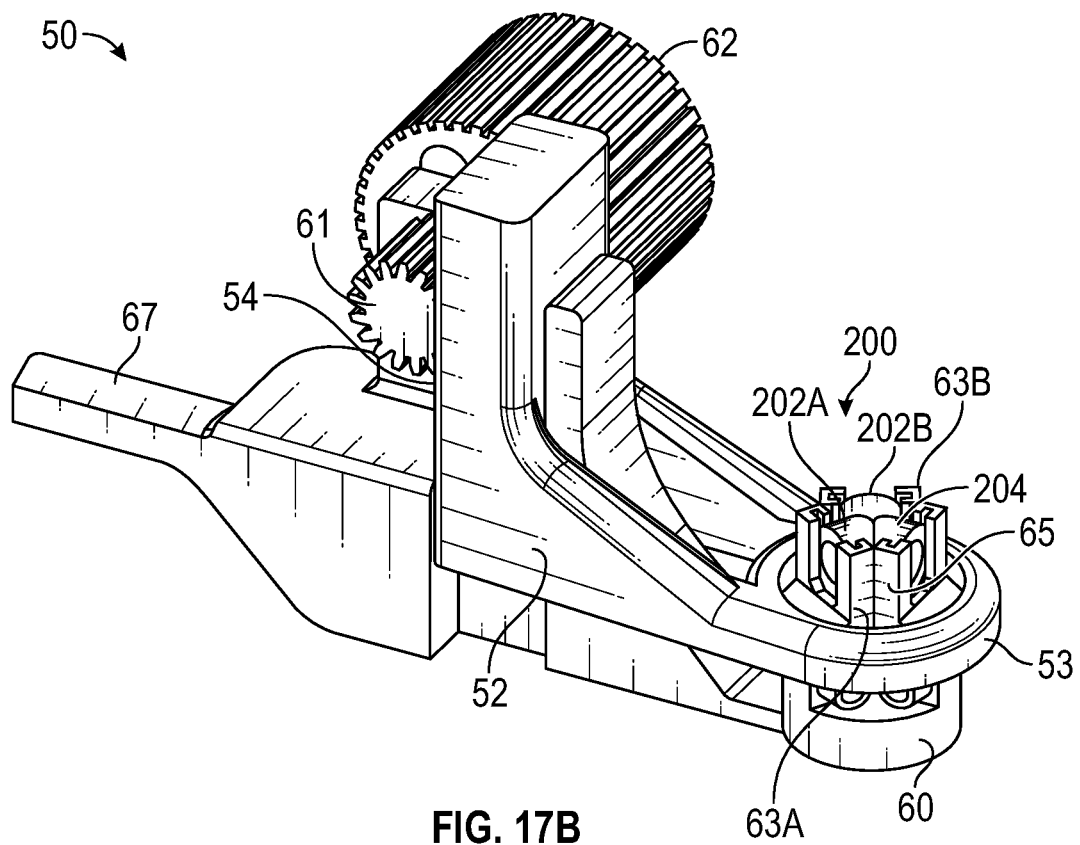

Further, the first receiving coupler ring 202A (second receiving coupler ring 202B/donor coupler ring 204) defines a peripheral surface 232A (232B/252) that includes a pair of slots 233A (233B/253) for engagement with a coupler device 50 (FIGS. 17A and 17B). The first receiving coupler ring 202A (second receiving coupler ring 202B/donor coupler ring 204) additionally includes a rear face (not shown for first receiving coupler ring 202A) defined opposite to the wedged face 221A (221B/241). Rear faces 231B and 251 of the second receiving coupler ring 202B and donor coupler ring 204 are visible in FIG. 15. In the embodiment shown, the wedged face 221A (221B/241) defines a first (second/third) angle between the first face 222A (222B/242) and the second face 225A (225B/245); the value of the first (second/third) angle is 120 degrees.

The first receiving coupler ring 202A, the second receiving coupler ring 202B and the donor coupler ring 204 of the multi-way coupler ring assembly 200 are configured to be coupled together simultaneously. FIGS. 17A and 17B illustrate the coupler device 50 for coupling the components of the multi-way coupler ring assembly 200 during an end-to-side anastomosis procedure. The coupler device 50 defines a closure element 52 moveable within a body assembly 60. The body assembly 60 defines a first receiving arm 63A, a second receiving arm 63B, and a donor arm 65 that each respectively engage the first receiving coupler ring 202A, the second receiving coupler ring 202B and the donor coupler ring 204 and are separated by 120 degrees. In particular, the pair of arm slots 233A of the first receiving coupler ring 202A engage the first receiving arm 63A, the pair of arm slots 233B of the second receiving coupler ring 202B engage the second receiving arm 24B, and the pair of arm slots 253 of the donor coupler ring 204 engage the donor arm 65. In the embodiment shown, the first receiving arm 63A, second receiving arm 63B, and donor arm 65 each include a respective open portion 64A, 64B and 66 oriented at a distal portion of each respective first receiving arm 64A, second receiving arm 64B, and donor arm 65 for placement and removal of the multi-way coupler ring assembly 200 from the coupler device 50. The closure element 52 can include a loop portion 53 configured to engage and close the first receiving arm 64A, second receiving arm 64B, and donor arm 65 as shown in FIGS. 17A and 17B. Further, in some embodiments, the closure element 52 defines a rack portion 53 for engagement with a pinion 61 rotatable by a dial 62 that actuates the closure element 52 in a first direction A or an opposite second direction B.

In an open configuration illustrated in FIG. 17A, the loop portion 53 of the closure element 52 is positioned away from the first receiving arm 63A, second receiving arm 63B, and donor arm 65. In a closed configuration illustrated in FIG. 17B, the loop portion 53 of the closure element 52 draws the first receiving arm 63A, second receiving arm 63B, and donor arm 65 together as the closure element 52 is actuated in a vertical direction relative to the body assembly 60. As illustrated in FIG. 17C, this action couples the first receiving coupler ring 202A, the second receiving coupler ring 202B, and the donor coupler ring 204 together. Following coupling of the first receiving coupler ring 202A, the second receiving coupler ring 202B, and the donor coupler ring 204, the coupler device 50 can be removed. In some embodiments, the body assembly 60 includes a stabilizer flange 67 that is configured to be grasped by retractor 90 (FIG. 13) and can additionally provide an element for grasping by a practitioner.

Figure 18:
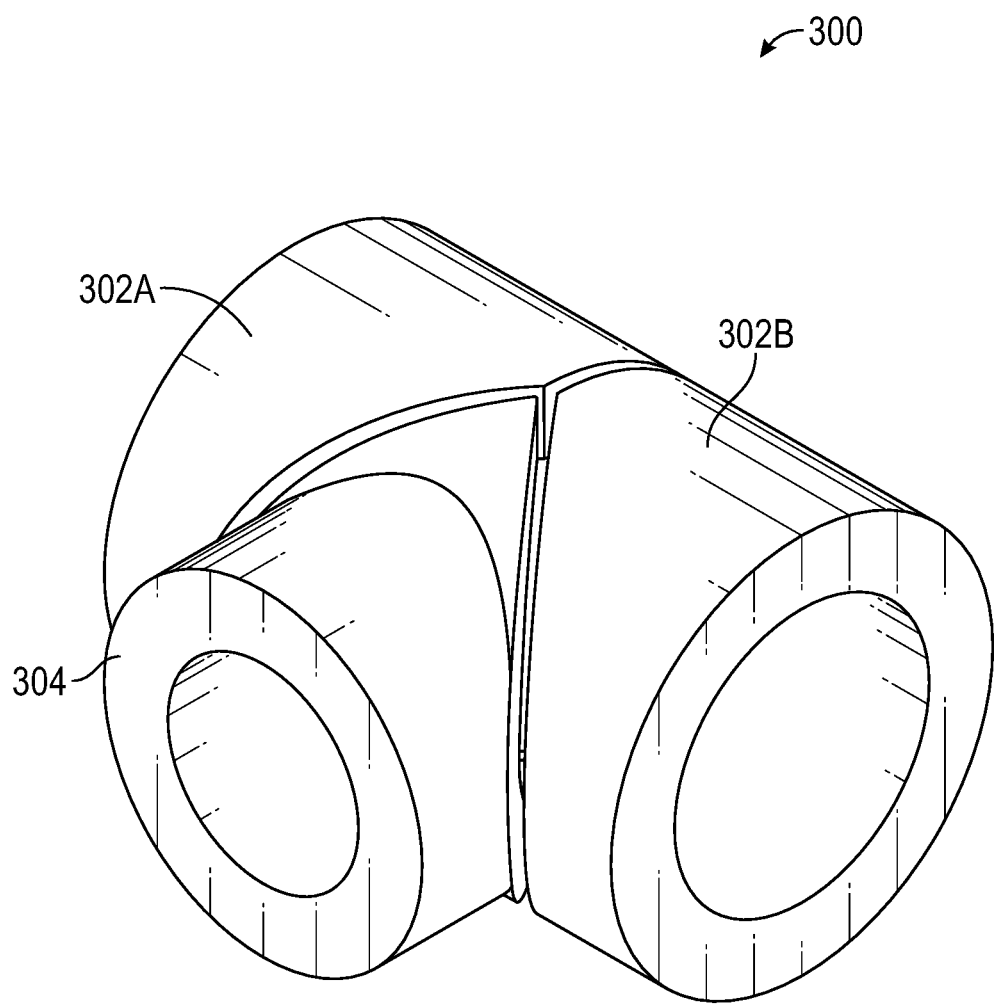
FIG. 18 is a perspective view showing a third embodiment of a multi-way coupler ring assembly.
Figure 19C:
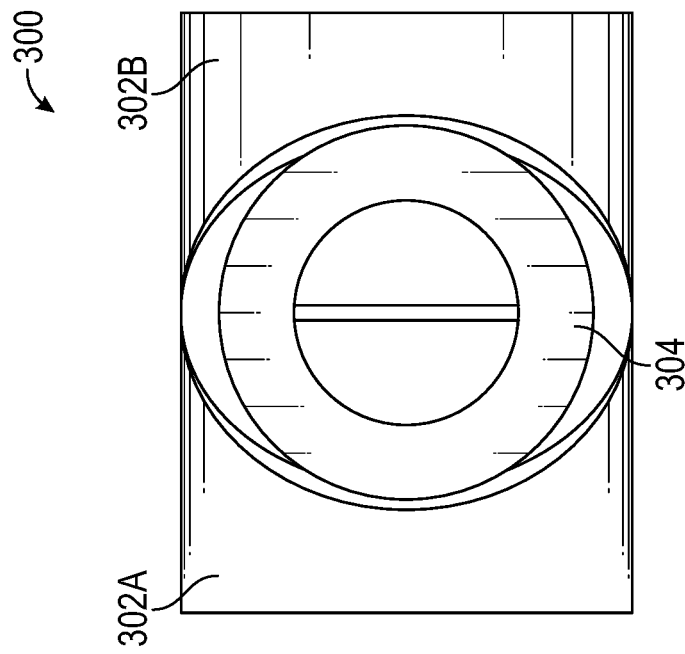
FIGS. 19A-19C is a series of illustrations showing the multi-way coupler ring assembly of FIG. 18.
Figure 19B:
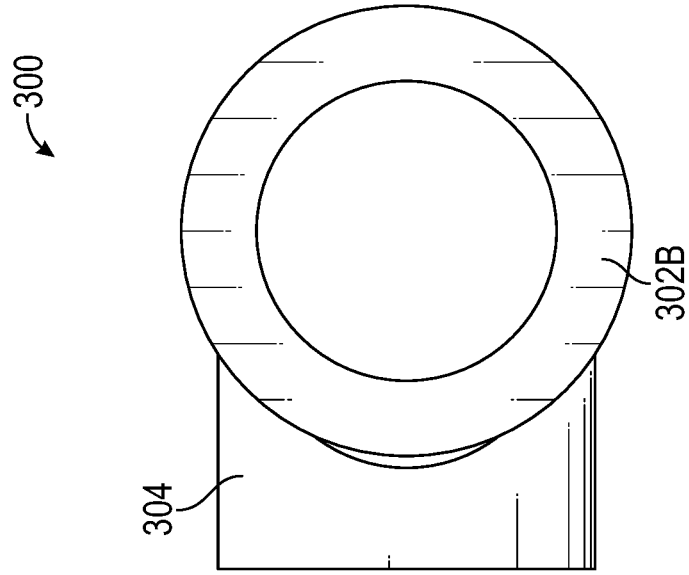
Figure 19A:
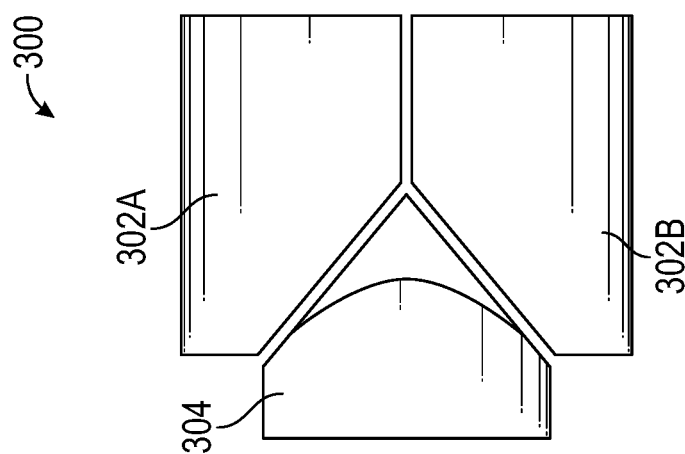

Referring to FIGS. 18-19C, an alternative multi-way coupler ring assembly 300 is illustrated in which a first, second and third angle of each respective first receiving coupler ring 302A, second receiving coupler ring 302B and donor coupler ring 304 are not equal and instead form a "T" shape. In the example shown, the first, second and third angles sum to 360 degrees. Further, in the example shown, the diameter of the donor coupler ring 304 can be smaller than that of the first receiving coupler ring 302A and the second receiving coupler ring 302B.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A ring coupler assembly comprising:
a first receiving coupler ring defining a wedged surface and a first channel defined axially through the wedged surface, the wedged surface including a first face and a second face that meet at a first apex of the first receiving coupler ring;
a second receiving coupler ring defining a wedged surface and a second channel defined axially through the wedged surface of the second receiving coupler ring, wherein the wedged surface of the second receiving coupler ring includes a first face and a second face that meet at a second apex of the second receiving coupler ring; and
a donor coupler ring defining a wedged surface and a third channel defined axially through the wedged surface of the donor coupler ring, wherein the wedged surface of the donor coupler ring includes a first face and a second face that meet at a third apex of the donor coupler ring;
wherein the first apex, the second apex, and the third apex meet to form a multi-way connection between the first channel, the second channel, and the third channel, wherein the second face of the second receiving coupler ring engages with the second face of the first receiving coupler ring, the first face of the donor coupler ring engages with the first face of the second receiving coupler ring, and the second face of the donor coupler ring engages with the first face of the first receiving coupler ring.

2. The ring coupler assembly of claim 1, wherein:
the first channel of the first receiving coupler ring is configured to receive a first receiving vessel;
the second channel of the second receiving coupler ring is configured to receive a second receiving vessel; and
the third channel of the donor coupler ring is configured to receive a donor vessel.

3. The ring coupler assembly of claim 1, wherein:
the wedged surface of the first receiving coupler ring includes a first plurality of pins and a second plurality of pins;
the wedged surface of the second receiving coupler ring includes a first plurality of pins and a second plurality of pins; and
the wedged surface of the donor coupler ring includes a first plurality of pins and a second plurality of pins.

4. The ring coupler assembly of claim 3, wherein each plurality of pins of the first receiving coupler ring, the second receiving coupler ring, and the donor coupler ring are configured to capture an everted vessel.

5. The ring coupler assembly of claim 3, wherein the first plurality of pins extending from the first face of the first receiving coupler ring and the first plurality of pins extending from the first face of the second receiving coupler ring are oriented towards the donor coupler ring.

6. The ring coupler assembly of claim 3, wherein the second plurality of pins extending from the second face of the first receiving coupler ring are perpendicular to the second face of the first receiving coupler ring and are each configured for engagement with a respective pin receptacle of the second face of the second receiving coupler ring.

7. The ring coupler assembly of claim 3, wherein the second plurality of pins extending from the second face of the second receiving coupler ring are perpendicular to the second face of the second receiving coupler ring and are each configured for engagement with a respective pin receptacle of the second face of the first receiving coupler ring.

8. The ring coupler assembly of claim 3, wherein the first and second plurality of pins extending from the first and second faces of the donor coupler ring are each perpendicular to their respective faces and are configured for respective engagement with a first plurality of pin receptacles of the first face of the first receiving coupler ring and a first plurality of pin receptacles of the first face of the second receiving coupler ring.

9. The ring coupler assembly of claim 3, wherein the first and second plurality of pins respectively extending from the first and second faces of the first receiving coupler ring, second receiving coupler ring and donor coupler ring are each perpendicular to their respective faces.

10. The ring coupler assembly of claim 3, wherein each pin of the first and second plurality of pins of the first receiving coupler ring, second receiving coupler ring and donor coupler ring are deformable.

11. The ring coupler assembly of claim 1, wherein:
the wedged surface of the first receiving coupler ring includes a first plurality of pin receptacles and a second plurality of pin receptacles;
the wedged surface of the second receiving coupler ring includes a first plurality of pin receptacles and a second plurality of pin receptacles; and
the wedged surface of the donor coupler ring includes a first plurality of pin receptacles and a second plurality of pin receptacles.

12. The ring coupler assembly of claim 11, wherein the second plurality of pin receptacles of the second face of the first receiving coupler ring are each configured for engagement with a respective pin of a first plurality of pins of the first face of the second receiving coupler ring.

13. The ring coupler assembly of claim 11, wherein the second plurality of pin receptacles of the second face of the second receiving coupler ring are each configured for engagement with a respective pin of a second plurality of pins of the second face of the first receiving coupler ring.

14. The ring coupler assembly of claim 11, wherein the first plurality of pin receptacles of the first face of the first receiving coupler ring and the first plurality of pin receptacles of the first face of the second receiving coupler ring are each configured for engagement with a respective second plurality of pins of the second face of the donor coupler ring and a first plurality of pins of the first face of the donor coupler ring.

15. The ring coupler assembly of claim 14, wherein the first plurality of pins of the first face of the donor coupler ring and the second plurality of pins of the second face of the donor coupler ring define a bent configuration and wherein the first plurality of pin receptacles of the first face of the first receiving coupler ring and the first plurality of pin receptacles of the first face of the second receiving coupler ring define a notched configuration to receive the first plurality of pins of the first face of the donor coupler ring and the second plurality of pins of the second face of the donor coupler ring.

16. The ring coupler assembly of claim 11, wherein the first plurality of pin receptacles of the first face of the donor coupler ring and the second plurality of pin receptacles of the second face of the donor coupler ring are each configured for respective engagement with a first plurality of pins of the first face of the second receiving coupler ring and with a first plurality of pins of the first face of the first receiving coupler ring.

17. The ring coupler assembly of claim 1, wherein the respective channels of the first receiving coupler ring, the second receiving coupler ring and the donor coupler ring each define an elliptical cross-section.

18. The ring coupler assembly of claim 1, wherein:
the first face and the second face of the wedged surface of the first receiving coupler ring define a first angle;
the first face and the second face of the wedged surface of the second receiving coupler ring define a second angle; and
the first face and the second face of the wedged surface of the donor coupler ring define a third angle.

19. The ring coupler assembly of claim 18, wherein the first angle, the second angle, and the third angle are each nonzero and wherein the first angle, the second angle, and the third angle sum to 360 degrees.

20. A system, comprising:
a multi-way ring coupler assembly, including:
a first receiving coupler ring defining a wedged surface and a channel defined axially through the wedged surface;
a second receiving coupler ring defining a wedged surface and a channel defined axially through the wedged surface of the second receiving coupler ring, wherein the second receiving coupler ring is configured for engagement with the first receiving coupler ring; and
a donor coupler ring defining a wedged surface and a channel defined axially through the wedged surface of the donor coupler ring, wherein the donor coupler ring is configured for engagement with the second receiving coupler ring and the first receiving coupler ring; and
a coupler device defining a first receiving arm that receives the first receiving coupler ring, a second receiving arm that receives the second receiving coupler ring, and a donor arm that receives the donor coupler ring, wherein the coupler device is configured to couple the first receiving coupler ring, the second receiving coupler ring and the donor coupler ring by:
actuating the first receiving arm and the second receiving arm into a closed position such that the first receiving coupler ring and the second receiving coupler ring are coupled together; and
actuating the donor arm into a closed position such that the donor coupler ring, the first receiving coupler ring and the second receiving coupler ring are coupled together.

21. The system of claim 20, wherein the wedged surface of each respective first receiving coupler ring, second receiving coupler ring, and donor coupler ring includes a first face and a second face that meet at an apex.

22. The system of claim 21, wherein actuating the first receiving arm and the second receiving arm into the closed position causes the second face of the first receiving coupler ring to couple with the second face of the second receiving coupler ring.

23. The system of claim 21, wherein actuating the donor arm into the closed position causes the first face of the donor coupler ring to couple with the first face of the second receiving coupler ring and causes the second face of the donor coupler ring to couple with the first face of the first receiving coupler ring.

* * * * *